(12) United States Patent
Parr et al.

(10) Patent No.: US 12,394,516 B2
(45) Date of Patent: Aug. 19, 2025

(54) EFFICIENT STORAGE OF DRUG LIBRARY EDITOR ENTRIES

(71) Applicant: CareFusion 303, Inc., San Diego, CA (US)

(72) Inventors: Richard Anthony Parr, San Deigo, CA (US); Russell McDaniel, San Diego, CA (US); Andrew S. Ergeson, San Diego, CA (US); Claire Ellen Knight, Arlington, TX (US)

(73) Assignee: CAREFUSION 303, INC., San Diego, CA (US)

( * ) Notice: Subject to any disclaimer, the term of this patent is extended or adjusted under 35 U.S.C. 154(b) by 169 days.

(21) Appl. No.: 18/251,688

(22) PCT Filed: Nov. 2, 2021

(86) PCT No.: PCT/US2021/057780
§ 371 (c)(1),
(2) Date: May 3, 2023

(87) PCT Pub. No.: WO2022/098676
PCT Pub. Date: May 12, 2022

(65) Prior Publication Data
US 2023/0420120 A1 Dec. 28, 2023

Related U.S. Application Data

(60) Provisional application No. 63/109,275, filed on Nov. 3, 2020.

(51) Int. Cl.
*G16H 40/40* (2018.01)
*G06F 16/11* (2019.01)
*G16H 10/00* (2018.01)

(52) U.S. Cl.
CPC .......... *G16H 40/40* (2018.01); *G06F 16/128* (2019.01); *G16H 10/00* (2018.01)

(58) Field of Classification Search
None
See application file for complete search history.

(56) References Cited

U.S. PATENT DOCUMENTS

| 5,416,695 A | 5/1995 | Stutman et al. |
| 5,681,285 A | 10/1997 | Ford et al. |

(Continued)

OTHER PUBLICATIONS

Stirbu et al. ("Towards Agile Yet Regulatory-Compliant Development of Medical Software," 2018 IEEE International Symposium on Software Reliability Engineering Workshops (ISSREW), Memphis, TN, USA, 2018, pp. 337-340) (Year: 2018).*

(Continued)

*Primary Examiner* — Christopher B Tokarczyk
(74) *Attorney, Agent, or Firm* — MASCHOFF BRENNAN

(57) ABSTRACT

The disclosed systems and methods provide an efficient solution to manage the entries of versioned libraries. A method includes receiving a request to modify an entry corresponding to a numerically-versioned library or a related master. The method includes obtaining a first snapshot record for the entry corresponding to the library or the master. The method includes receiving user changes to data of the entry. The method also includes generating a second snapshot record for the entry. The second snapshot record capturing the user changes and having an assigned second plurality of version identification values. The method further includes updating the first plurality of version identification values of the first snapshot record based on assigned values of the second plurality of version identification values of the second snapshot record. The first and second plurality of (Continued)

version identification values indicating that the first snapshot record precedes the second snapshot record.

20 Claims, 19 Drawing Sheets

(56) References Cited

U.S. PATENT DOCUMENTS

| | | |
|---|---|---|
| 5,713,856 A | 2/1998 | Eggers et al. |
| 2018/0217851 A1* | 8/2018 | Sirajuddin .......... G06F 9/44521 |
| 2019/0087130 A1* | 3/2019 | Lee ..................... G06F 16/2358 |
| 2020/0226326 A1* | 7/2020 | Ros ......................... H04L 69/26 |
| 2020/0293916 A1* | 9/2020 | Li ........................... G06F 9/5072 |
| 2021/0125713 A1* | 4/2021 | Audrain ................. G16H 40/40 |

OTHER PUBLICATIONS

Anonymous: "Linked list—Wikipedia", Oct. 24, 2020, pp. 1-20; Retrieved from https://en.wikipedia.org/w/index.php?title=Linked_list&olidid=985263131 [retrieved on Jan. 27, 2022].

International Search Report of Application No. PCT/US2021/057780, mailed Feb. 7, 2022, 3 pages.

International Search Report and Written Opinion for Application No. PCT/US2021/057780, dated Feb. 7, 2022, 17 pages.

Qiu et al., "A survey of machine learning for big data processing", EURASIP Journal on Advances in Signal Processing, May 28, 2016, Article No. 67 (2016), https://doi.org/10.1186/s13634-016-0355-x.

* cited by examiner

900

902
Store one or more numerically-versioned libraries associated with a medical device, the one or more numerically-versioned libraries comprising available configuration data associated with programming the medical device

904
Receive a first request to modify an entry corresponding to a respective numerically-versioned library

906
Obtain, responsive to receiving the first request, at least a first snapshot record for the entry, the first snapshot record including a first plurality of version identification values

908
Receive user changes to data of the entry

910
Generate, responsive to receiving the user changes, a second snapshot record, where generating the second snapshot record includes capturing the user changes to the data of the entry, and assigning a second plurality of version identification values to the second snapshot record

912
Update the first plurality of version identification values of the first snapshot record based on assigned values of the second plurality of version identification values of the second snapshot record such that the first snapshot record is identified as preceding the second snapshot record

914
Store the first snapshot record and the second snapshot record in association with the respective numerically-versioned library

916
Receive, in connection with programming the medical device, a second request to access a numbered version of the respective library (A)

Figure 9A

EFFICIENT STORAGE OF DRUG LIBRARY EDITOR ENTRIES

CROSS REFERENCE TO RELATED APPLICATIONS

This application claims the benefit of International Application No. PCT/US2021/057780, entitled "EFFICIENT STORAGE OF DRUG LIBRARY EDITOR ENTRIES," filed on Nov. 2, 2021, which claims the benefit of U.S. Provisional Application Ser. No. 63/109,275, filed on Nov. 3, 2020, the entireties of both which are incorporated herein.

TECHNICAL FIELD

The present disclosure generally relates to databases, and more specifically relates to methods and systems for providing efficient storage of drug library editor entries.

BACKGROUND

To provide flexibility in accommodating different healthcare environments and treatment approaches, one or more drug library editor (DLE) applications may be provided. The DLE applications enable pharmacists and other medical professionals to create and modify various custom treatment regimens. To support change logs and to unambiguously resolve specific configurations for patient care, a DLE application may utilize a database that stores copies of all drug library versions. Each stored version may include a large number of drug library entries, infusion parameters, and other records, which may incur a large storage footprint exceeding available storage and processing capacity. Accordingly, there is a need for improved systems and methods for providing efficient storage of DLE entries.

SUMMARY

According to various implementations, a method for providing efficient storage of drug library editor entries is provided. A method may include storing one or more numerically-versioned libraries associated with a medical device. The one or more libraries include available configuration data associated with programming the medical device. The method may include receiving a first request to modify an (existing) entry corresponding to a configuration setup within a respective numerically-versioned library, and obtaining, responsive to receiving the first request, at least a first snapshot record (where the first snapshot is a previously generated snapshot record) for the setup entry. The first snapshot record includes a first plurality of version identification values. The method may further includes receiving user changes to data of the entry, and generating, responsive to receiving the user changes, a second snapshot record for the entry. Generating the second snapshot record includes capturing the user changes to the data of the entry, and assigning a second plurality of version identification values to the second snapshot record. The method may further include updating the first plurality of version identification values of the first snapshot record based on assigned values of the second plurality of version identification values of the second snapshot record such that the first snapshot record is identified as preceding the second snapshot record. The method may include storing the first snapshot record and the second snapshot record in association with the respective numerically-versioned library. The method may further include receiving, in connection with programming the medical device, a second request to access a numbered version of the respective numerically-versioned library, and identifying one or more records corresponding to the numbered version of the respective numerically-versioned library. The method may include providing, responsive to the second request, a copy of the one or more record corresponding to the numbered version of the respective numerically-versioned library to the medical device to cause the programming of the medical device.

In some implementations, updating the first plurality of version identification values of the first snapshot record based on assigned values of the second plurality of version identification values of the second snapshot includes assigning a start value of the second plurality of version identification values of the second snapshot record as an end value for first plurality of version identification values of the first snapshot record.

In some implementations, the first and second plurality of version identification values include one or more of a start date, end date, start library version number, and end library version number. In some implementations, the second plurality of version identification values include a user identifier for identifying a user that provided the first request. In some implementations, the first request to modify the entry is a request to update or delete the entry. In some implementations, a portion of the configuration data is shared among a subset of one or more numerically-versioned libraries under a related master.

In some implementations, the method may further include receiving a third request to generate an additional entry corresponding to the respective numerically-versioned library, receiving user input defining data of the additional entry, and generating a snapshot-parent record for the additional entry that includes data that does not change; and generating a snapshot record for the additional entry that includes data that can be modified by a user. The method may further include assigning a respective plurality of version identification values to the snapshot record of the additional entry.

In some implementations, the method may include receiving a fourth request to approve a library version corresponding to the respective numerically-versioned library. The method may include obtaining a current library version record corresponding to the numerically-versioned library, and updating a plurality of version identification values of the current library version record to identify the current library version record as approved. The method may further include generating a new library version record corresponding to the numerically-versioned library, and assigning a respective plurality of version identification values to the new library version record such that the new library version record is identified as a draft. In some implementations, updating the plurality of version identification values of the current library version record includes assigning a start value of the respective plurality of version identification values of the new library version record as an end value for plurality of version identification values of the current library version record.

In some implementations, the method may include receiving a fifth request to generate a new numerically-versioned library, and in response to receiving the fifth request, generating the new numerically-versioned library. The method may include generating a respective library version record for the new numerically-versioned library, and assigning a plurality of version identification values to the respective library version record. The method may further include generating a respective library version under-master snapshot record corresponding to an entry under a related master, and assigning a plurality of version identification values to the respective library version under-master snapshot record. In some implementations, the method may further include determining whether additional entries are associated under the master. The method may include, in accordance with a determination that additional entries are associated under the master, for each additional entry, generating an additional respective library version under-master snapshot record; and assigning a respective plurality of version identification values to the additional respective library version under-master snapshot record. In some implementations, the method may further include determining whether the new numerically-versioned library is to be pre-populated, and in accordance with a determination that the new numerically-versioned library is to be pre-populated, importing an existing entry corresponding to another numerically-versioned library; and assigning a plurality of version identification values to the imported entry.

According to various implementations, a method of managing one or more records for a medical device, includes storing one or more masters associated with a medical device. The one or more masters include configuration data associated with programming the medical device. The method may include receiving a first request to modify an entry corresponding to a respective master. The method may further include obtaining, responsive to receiving the first request, at least a first snapshot record for the entry. The first snapshot record includes a first plurality of version identification values. The method may further include receiving user changes to data of the entry. The method may include generating, responsive to receiving the user changes, a second snapshot record for the entry. Generating the second snapshot record includes capturing the user changes to the data of the entry, and assigning a second plurality of version identification values to the second snapshot record. The method may further include updating the first plurality of version identification values of the first snapshot record based on assigned values of the second plurality of version identification values of the second snapshot record such that the first snapshot record is identified as preceding the second snapshot record. The method may also include storing the first snapshot record and the second snapshot record in association with the respective master. The method may include receiving, in connection with programming the medical device, a second request to access an entry of the respective master, and identifying one or more records corresponding to the entry of the respective master. The method may further include providing, responsive to the second request, a copy of the one or more records corresponding to the entry of the respective master to the medical device to cause the programming of the medical device.

In some implementations, the method may further include after updating the first plurality of version identification values of the first snapshot record, generating a new library version under-master snapshot record for each numerically-versioned library that references the master. For each numerically-versioned library that references the master, the method may include receiving a current library version record for a numerically-versioned library, assigning a plurality of version identification values to the new library version under-master snapshot record based on the current library version record for the numerically-versioned library, assigning the new library version under-master snapshot record to the second snapshot record, and updating a plurality of version identification values of a previously-last library version under-master snapshot record, wherein the plurality of version identification values for the previously-last library version under-master snapshot record indicates that the previously-last library version under-master snapshot record precedes the new library version under-master snapshot record. In some implementations, the method may also include after generating the snapshot record of an additional master entry, generating a new library version under-master snapshot record for each numerically-versioned library that references the master. For each numerically-versioned library that references the master, the method may include receiving a current library version record for a numerically-versioned library, assigning a plurality of version identification values to the new library version under-master snapshot record based on the current library version record for the numerically-versioned library, and assigning the new library version under-master snapshot record to the snapshot record of the additional entry.

Other aspects include corresponding systems, apparatuses, and computer program products for implementation of the computer-implemented method.

Further aspects of the subject technology, features, and advantages, as well as the structure and operation of various aspects of the subject technology are described in detail below with reference to accompanying drawings.

DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

FIGS. 9A-9B are flowcharts illustrating a method for generating or modifying a record under a numerically-versioned library, according to various aspects of the subject technology.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

The subject technology includes a system and method for managing a data library for programming a medical device or medical system. In particular, the subject technology includes a system and method for managing versioning of a drug library specific to a medical device (such as an infusion pump) or other medical system. An existing drug library may be updated multiple times over its lifetime. When the library is updated the system stores the new state of the library, which may then be associated with a particular owner and/or version, and/or other data. The updated library may also be easily approved and stored for use on patients. Further, each different approved version of the library can be accessed by querying the one or more records. Further, the system and method described herein eliminate the need to copy the entire library between approved drug library versions.

Figure 1:
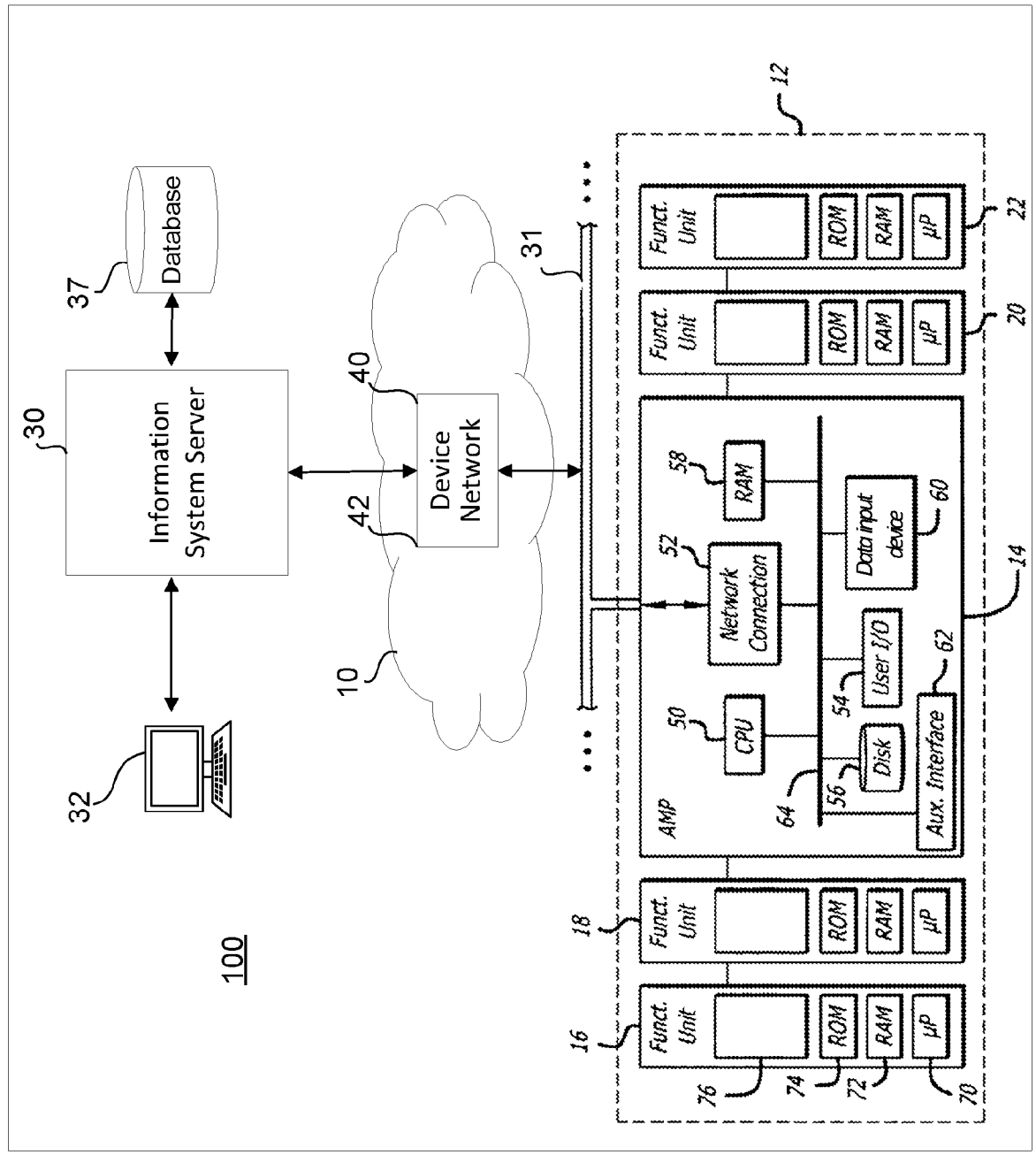
FIG. 1 depicts an example of an institutional patient care system 100 of a healthcare organization, according to various aspects of the subject technology.

FIG. 1 depicts an example of an institutional patient care system 100 of a healthcare organization, according to aspects of the subject technology. In FIG. 1, a patient care device (or "medical device" generally) 12 is connected to a hospital network 10. The term patient care device (or "PCD") may be used interchangeably with the term point-of-care unit (or "PCU"), either which may include various ancillary medical devices such as an infusion pump, a vital signs monitor, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which patient care devices 12 (and other devices) communicate in accordance with normal operations.

Additionally, institutional patient care system 100 may incorporate a separate information system server 30, the function of which will be described in more detail below. Moreover, although the information system server 30 is shown as a separate server, the functions and programming of the information system server 30 may be incorporated into another computer, if such is desired by engineers designing the institution's information system. Institutional patient care system 100 may further include one or multiple device terminals 32 for connecting and communicating with information system server 30. Device terminals 32 may include personal computers, personal data assistances, mobile devices such as laptops, tablet computers, augmented reality devices, or smartphones, configured with software for communications with information system server 30 via network 10.

Patient care device 12 comprises a system for providing patient care, such as that described in U.S. Pat. No. 5,713,856 to Eggers et al. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54 (e.g., a display screen and/or keyboard), a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PC MCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system or located externally and communicating with pharmacy system through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with interface unit 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may also be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1, any number of devices may be connected directly or indirectly to central interface unit 14. The number and type of functional modules described herein are intended to be illustrative, and in no way limit the scope of the subject technology. Module-specific components 76 include any components necessary for operation of a particular module, such as a pumping mechanism for infusion pump module 16.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. Each mode or personality may include a different set of configuration parameters, or implement a different drug library, as described below. The configuration database may be stored on disk 56 (or database) internal to patient care device 12, or may be an external database 37. A particular configuration database (or portion thereof) may be selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 12 location in the hospital or hospital computer network 10. Patient care information may be entered through interface device 52, 54, 60 or 62, and may originate from anywhere in network 10, such as, for example, from a pharmacy server, admissions server, laboratory server, and the like.

An interface unit 14 of patient care device 12 also has access to a drug library. Further information on drug libraries is contained in U.S. Pat. No. 5,681,285 to Ford. The drug library may be resident in the controller, in a local accessible memory, or may be located elsewhere on the system network but be accessible by the controller. "Drug Library Profiles" may be established in which medications (e.g., drugs), concentrations, and other pumping parameters are set particular to that type of care—such as, for example, an ICU (intensive care unit) profile, a pediatric profile, a neonatal profile and others. Data sets of medications allowed for use and configurations of pumping parameters including limitations for that use may be available for each drug library profile. As such, drug library profiles may, although not necessarily, correspond to different types of patient care. Thus, an interface unit 14 located in a pediatric ward, for example, may utilize a pediatric drug library profile that includes sets of allowed medications, pumping parameters, and pumping limitations that are specific to patients classified as pediatric or located in a pediatric ward. Similarly, an interface unit 14 located in an ICU may utilize an ICU drug library profile that includes a different set of allowed medications, pumping parameters, and pumping limitations that are specific to patients located in an intensive care environment and other patients requiring intensive care.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 52 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in information system server 30, decision support, remote data server, hospital department or unit stations, or within patient care device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

Figure 2:
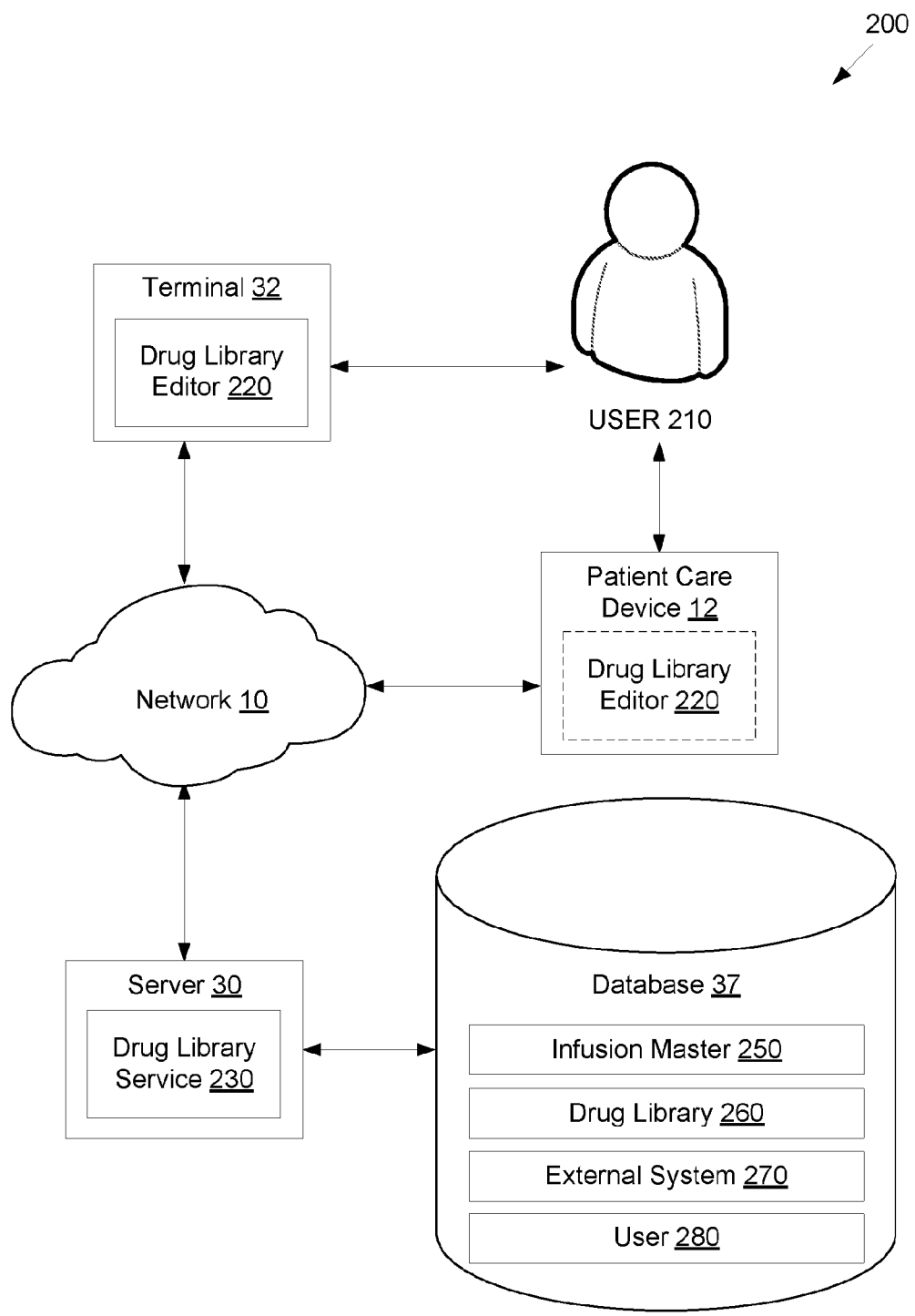
FIG. 2 illustrates a drug library editor system, according to various aspects of the subject technology.

FIG. 2 illustrates a drug library editor system 200 in accordance with some implementations. The drug library editor system 200 includes a device terminal 32, patient care device 12, network 10, server 30, and external database 37. A user 210 interacts with the device terminal 32 to access a drug library editor (DLE) 220. The DLE 220 allows the user 210 to modify or generate one or more infusion masters 250 and/or drug libraries 260 as discussed below in reference to FIGS. 3B-8. Alternatively or additionally, in some implementations, the user 210 accesses the DLE 220 directly from the patient care device 12. In some implementations, the device terminal 32 (and/or patient care device 12) is communicatively coupled to the server 30.

In some implementations, the server 30 includes a drug library service 230. The drug library service 230 provides the user 210 with access to an external database 37 that includes one or more infusion masters 250, drug libraries 260, external system 270 records, and/or user 280 records. In some implementations, the drug library service 230 maintains a history of modifications made to the one or more infusion masters 250 and/or drug libraries 260. In some implementations, the history of modifications to the one or more infusion masters 250 and/or drug libraries 260 is maintained by one or more records under the one or more infusion masters 250 and/or drug libraries 260 (as discussed below with reference to FIGS. 3A and 3B). In some implementations, a record "under" an infusion master 250 and/or drug library 260 is an individual data file that makes up and/or defines all or part of the infusion master 250 and/or drug library 260. Additionally, a record under an infusion master 250 and/or drug library 260 is directly or indirectly associated (or linked) to a single infusion master 250 or drug library 260. More specifically, each entry within an infusion master 250 and drug library 260 is part of respective hierarchical data scheme with a nested structure of entries, where each entry consists of parent record and a snapshot record. Additional information on the data structure is provided below in reference to FIG. 3B. In some implementations, the user 280 records are used to identify a user 210 operating the DLE 220 and track user specific modifications to infusion masters 250 and/or drug libraries 260. Any number of users 210 that are authorized to modify an infusion master 250, drug library 260, and/or related records can be added to the user 280 table. Alternatively or additionally, in some implementations, the one or more infusion masters 250, drug libraries 260, external systems 270 records, and/or user 280 records are stored locally on the device terminal 32 and/or on the patient care device 12 (e.g., internal database on disk 56).

Figure 3A:
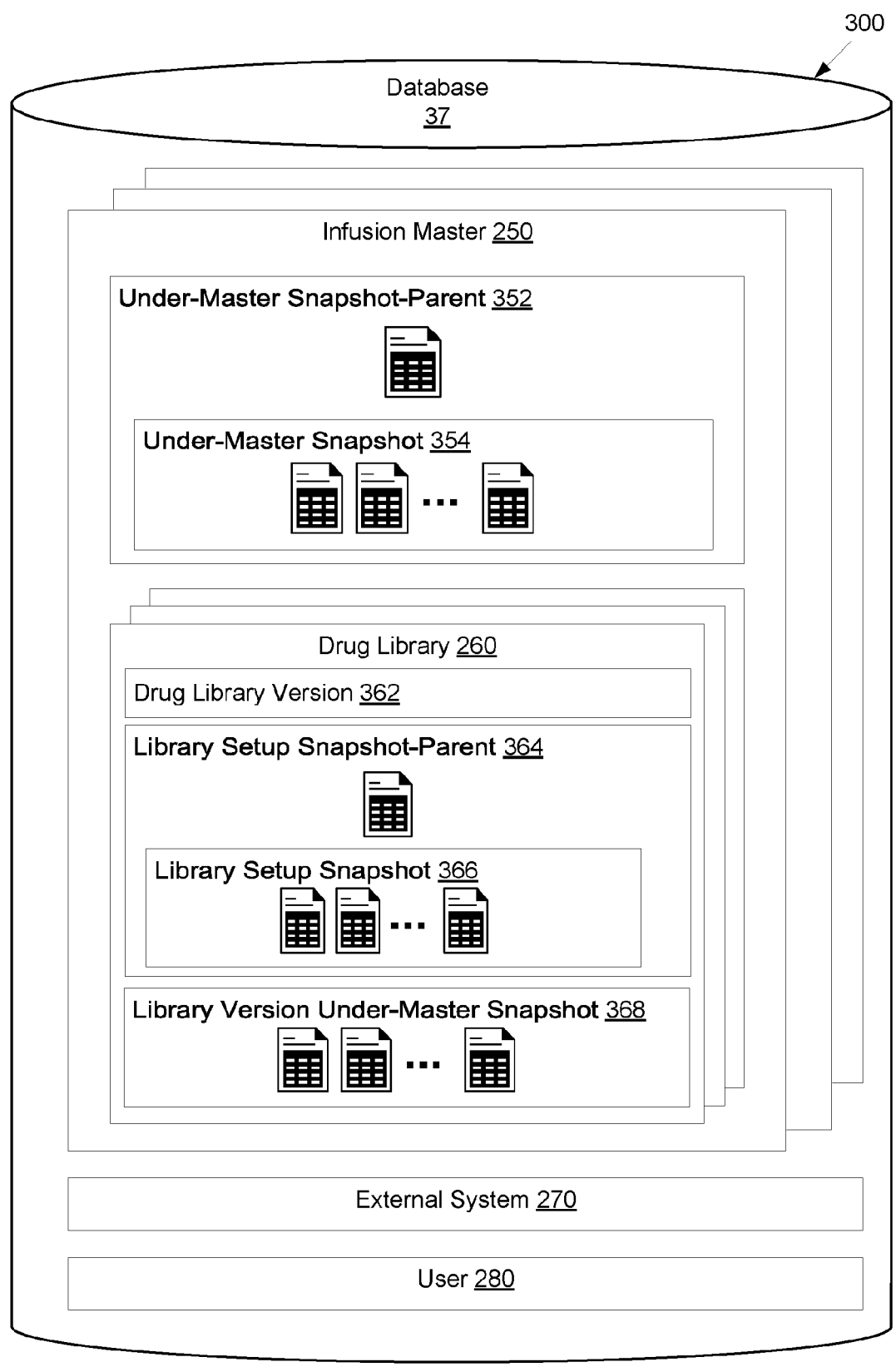
FIGS. 3A-3B illustrate an overview and data scheme of library records, according to various aspects of the subject technology.

Turning now to FIG. 3A, an overview of the drug library editor records 300 is illustrated in accordance with some implementation. The overview of the drug library editor records 300 includes external database 37 including records associated with one or more infusion masters 250, records associated with one or more drug libraries 260, external system 270 records, and/or user 280 records. These records include snapshot records that allow for the unambiguous capture of the state of each drug library version through the use of a versioning scheme that is applied to the snapshot data structures employed within the drug libraries 260, and through the use of data structures that capture version history for infusion masters 250, in such a manner that obviates the need to create copies each time that a version of a drug library is approved or created.

Entries, as used herein, include at least a pair of tables that include the overall parent record and a snapshot version of that entry, known as the snapshot record. The snapshot records include a plurality of version identification values. A non-exhaustive list of the plurality of version identification values includes 'Start Date Time,' 'End Date Time,' 'Start Library Version Number,' 'End Library Version Number.' In some implementation, the plurality of version identification values for the snapshot records further include a user identifier, initial state flag (for identifying the state of an infusion master and state of the library when a library is first created), delete flag (for conceptually deleting an entry). The snapshot records include various other attributes that contain business data (e.g., conceptual, task-domain information of direct relevance to the people using the solution or configuration). Parent records ("snapshot-parents") can further include data that does not change or data where there is no need to track history. Each snapshot-parent record has exactly one snapshot record where 'End Date Time' is null and, if present, 'End Library Version Number' is null. As such, a snapshot-parent record does not have a plurality of version identification values. Updates to the plurality of version identification values of one or more snapshot records are discussed below with reference to FIGS. 3B-8.

Each infusion master 250 is used to configure a patient care device 12 as specified by a user 210. An infusion master 250 can be related to one or more drug libraries (via a link from a drug library 260 record). In some implementations, each infusion master 250 is associated with one or more external systems (e.g. via external system 270 records) or none. In some implementations, the overall infusion master 250 includes one or more entry types, for such entries as drug or fluid entries; clinical advisory entries; therapy entries; drug concentration entries; and/or alias entries. Each drug or fluid can have many aliases, with each alias being associated with a single external system. Further, each drug can have many concentrations. As such, the different entry types of the overall infusion master 250 efficiently enable a user 210 to configure the patient care device 12 as needed.

Records under each infusion master 250 record include one or more under-master snapshot-parent 352 records. An under-master snapshot-parent 352 record is associated (or linked) to one or more under-master snapshot 354 records, and/or zero, one or more library version under-master snapshot 368 records (discussed below). For the purposes of this disclosure, each of these records are considered (indexed or linked) under an infusion master 250. For example, each record may be stored in database 37 in association with a respective infusion master 250, such that the record may be identified based on an indexing of the infusion master 250.

Each under-master snapshot 354 record includes a plurality of version identification values and non-parent data (e.g., data that can be changed and history tracked). Each under-master snapshot 354 record is directly linked to its corresponding under-master snapshot-parent 352 record, and to one library version under-master snapshot 368 record for each drug library 260 that associated with the infusion master 250. In this way, the different versions of a drug library 260 are synchronized with an infusion master 250. In other words the data structure scheme (described below with reference to FIG. 3B) allows for the efficient use of different records without having to duplicate entire record sets for an infusion master 250 and drug library version 362.

Each drug library 260 is used to configure a patient care device 12 for some drugs and/or fluids as specified by a user 210. Each drug library 260 record is linked to a single infusion master 250 record. In some implementations, a drug library 260 includes one or more entry types, for such entries as care type setup entries; drug or fluid setup entries; therapy setup entries; infusion setup entries; and/or concentration setup entries. Each drug library 260 can have many care type setups. Each care type setup can have many drug or fluid setups, with each drug or fluid setup being identified through the combination of a care type setup entry and drug or fluid entry. Each drug or fluid setup can have many therapy setups, with each therapy setup being identified through the combination of drug or fluid setup entry and therapy entry. Each therapy setup can have a few infusion setups, with each infusion setup being identified through the combination of a therapy setup entry and a dose mode (such as weight based, body-service-area based, or independent of both weight and body service area). Each infusion setup can have many concentration setups, with each concentration setup being identified through the combination of an infusion setup entry and a concentration entry. Different drug library 260 allow a user 210 to efficiently configure the patient care device 12 for different drugs and/or fluids as needed.

Records under each drug library 260 record include one or more drug library version 362 records, drug library setup data (pairs of library setup records), and library version under-master snapshot 368 records (referenced above and discussed in detail below). For the purposes of this disclosure, each of these records are considered (indexed or linked) under a drug library 260 record. For example, each record may be stored in database 37 in association with a respective drug library 260 record, such that the stored record may be identified based on an indexing of the drug library 260 record.

A drug library version 362 record is linked to a single drug library 260 record. Many drug library version 362 records can be linked to a single drug library 260 record. Each drug library version 362 record includes a plurality of version identification values. The plurality of version identification values for each drug library version 362 record includes an identifier for indicating whether the drug library version 362 record is an approved record or draft record. Approved drug library versions 362 can be used to configure a patient care device 12 for use on patients; however use of draft drug library versions 362 is limited (e.g., draft versions cannot be used on patients). After a drug library version 362 record is approved, the user (e.g., user 210) that approved the drug library version 362 record is assigned to the user identifier of the plurality of version identification values as the approver (e.g., a record from the user 280 table is linked to the approved drug library version 362 record).

The drug library setup data includes pairs of library setup tables, these tables being library setup snapshot-parent 364 and library setup snapshot 366. In some implementations, one or more of the library setup snapshot-parent 364 tables and library setup snapshot 366 tables are nested. Each library setup snapshot 366 record includes a plurality of version identification values. Each of the library setup snapshot-parent 364 records and/or library setup snapshot 366 records corresponds to a single drug library 260 record. In other words, each drug library 260 record has its own library setup snapshot-parent 364 records and library setup snapshot 366 records. Each library setup snapshot 366 record is linked to a corresponding library setup snapshot-parent 364 record.

Each external system 270 record includes data on one healthcare information system, such as an Electronic Medical Record (EMR) system. Each external system 270 record can be linked with many infusion master 250 records. In some implementations, data included in the infusion masters 250 and/or drug libraries 260 is based on the external system 270 records. (Each alias is associated with a specific external system 270 record, because different EMR systems can use the same identifier to refer to different drugs or fluids.)

Each user 280 record includes information identifying a user 210. Each user 280 record is associated with a particular user or user account. Each user 280 record is used to associate a particular user 210 to one or more records under an infusion master 250 and/or drug library 260 as described herein. In this way, the system maintains a full history of changes by identifying and linking a user 280 record to any generated, edited, deleted, and/or otherwise modified entry under an infusion master 250 and/or drug library 260.

Figure 3B:
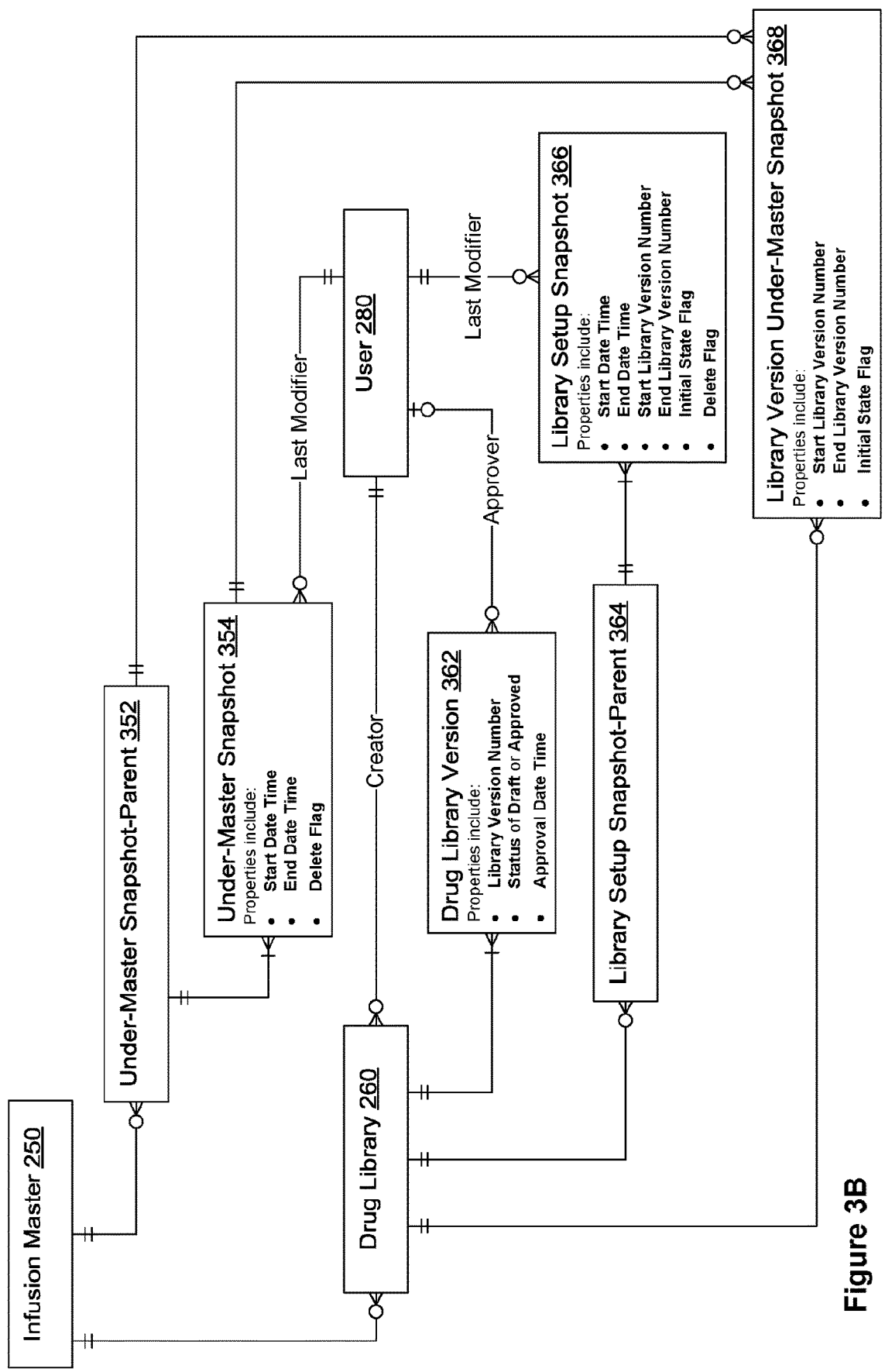

FIG. 3B illustrates the associated relationships between an infusion master 250 record, drug library 260 record, and other records in accordance with some implementations. One or more infusion master 250 records, under-master snapshot-parent 352 records, under-master snapshot 354 records, drug library 260 records, drug library version 362 records, library setup snapshot-parent 364 records, library setup snapshot 366 records, library version under-master snapshot 368 records, and user 280 records can be associated with each other via one or more links as described below. Each of the one or more links is stable, that is, once a link is assigned to a given record, the link never changes which other-record it references. For example, a drug library 260 record linked to an infusion master 250 record cannot change or alter to which infusion master 250 record it is related.

Each infusion master 250 record is associated with zero, one, or many under-master snapshot-parent 352 records, and/or zero, one, or many drug library 260 records. Alternatively, each under-master snapshot-parent 352 record and each drug library 260 record is associated with exactly one infusion master 250 record.

Each under-master snapshot-parent 352 record is associated with one or more under-master snapshot 354 records, and/or zero, one, or many library version under-master snapshot 368 records. Alternatively, each under-master snapshot 354 record is associated with exactly one under-master snapshot-parent 352 record. Similarly, each library version under-master snapshot 368 record is associated with exactly one under-master snapshot-parent 352 record. As mentioned above, an under-master snapshot-parent 352 record is not changed when a user 210 modifies (updates or logically deletes) an under-master entry. Further, an under-master snapshot-parent 352 record is generated by a user 210 when a new under-master entry is generated. The generation of an under-master snapshot-parent 352 record is described below with reference to FIG. 4.

Each under-master snapshot 354 record is associated with zero, one, or many library version under-master snapshot 368 records. Alternatively, each library version under-master snapshot 368 record is associated with exactly one under-master snapshot 354 record. Further, each under-master snapshot 354 record is associated with exactly one user 280 record (representing the user 210 who modified or generated the under-master entry thereby causing the under-master snapshot 354 record to be generated). Alternatively, each user 280 record can be associated with zero, one or many under-master snapshot 354 records (i.e., each user 210 is capable of modifying and/or generating many under-master entries).

When an under-master entry is modified or generated, the data within the under-master snapshot 354 table is altered based on user input, adhering to the following rules: On generation of a new entry, a new under-master snapshot 354 record is created, and on modification (update or logical deletion) of an entry, a new under-master snapshot 354 record is generated and the last under-master snapshot 354 record's plurality of version identification values are updated. On snapshot generation (for either entry generation or modification) a 'Start Date Time,' 'End Date Time,' and 'Delete Flag' of the plurality of version identification values of the new under-master snapshot 354 record are assigned. On update of the last under-master snapshot 354 record (when entry modification occurs), the 'End Date Time' is changed from null to the current date time. The specific assignments to the plurality of version identification values of the under-master snapshot 354 record are described below in FIGS. 4, 5A-5B, and 7.

A drug library 260 record is associated with one or more drug library version 362 records; zero, one, or many library setup snapshot-parent 364 records; zero, one, or many library version under-master snapshot 368 records; and exactly one user record 280 (for the purpose of identifying the creator of the drug library). Alternatively, each drug library version 362 record, library setup snapshot-parent 364 record, and library version under-master snapshot 368 record is associated with exactly one drug library 260 record. Additionally, each user 280 record can be associated, for the purpose of creation, with zero, one or more drug library 260 records.

Each drug library version 362 record is associated, for the purpose of approval, with zero or no more than one user 280 record. In other words, only a single user 210 is able to approve a drug library version 362 for use (the user 210 identified via their respective user 280 record). Alternatively, each user 280 record can be associated, for the purpose of approval, with zero, one or more drug library version 362 records. When a drug library version 362 record is approved, a plurality of version identification values of the drug library version 362 record is updated. In particular, 'Status' (e.g., DRAFT or APPROVED), and 'Approval Date Time' of the plurality of version identification values of the drug library version 362 are updated. In addition, a new drug library version 362 is created in a DRAFT 'Status', with a subsequent 'Library Version Number' (e.g., one value greater than the 'Library Version Number' of the last drug library version 362). In some implementations, the plurality of version identification values of the drug library version 362 record include a 'Start Date Time' and/or 'End Date Time.' The specific changes to the plurality of version identification values of the drug library version 362 record are described below in FIG. 6.

Each library setup snapshot-parent 364 record is associated with one or more library setup snapshot 366 records. Alternatively, each library setup snapshot 366 record is associated with exactly one library setup snapshot-parent 364 record. Further, each library setup snapshot 366 record is associated with exactly one user record 280 (representing the user 210 who modified or generated the library setup entry causing the library setup snapshot 366 record to be generated). Additionally, each user 280 record can be associated with zero, one or many library setup snapshot 366 records (i.e., each user 210 can modify or generate many library setup entries). Similar to an under-master snapshot-parent 352, a library setup snapshot-parent 364 record does not change when a user 210 updates one or more entries. Further, a library setup snapshot-parent 364 record can be generated by a user 210. The generation of a library setup snapshot-parent 364 record is described below with reference to FIG. 4.

When a library setup entry is modified or generated, the data within the library setup snapshot 366 table is altered based on user input, adhering to the following rules: On generation of a new entry, a new library setup snapshot 366 record is created, and on modification (update or logical deletion) of an entry, a new library setup snapshot 366 record is generated and the last library setup snapshot 366 record's plurality of version identification values is updated. On snapshot generation (for either entry generation or modification) a 'Start Date Time,' 'End Date Time,' 'Start Library Version Number', 'End Library Version Number,' 'Initial State Flag,' and 'Delete Flag' of the plurality of version identification values of the new library setup snapshot 366 record are assigned. On update of the last library setup snapshot 366 record (when entry modification occurs), the 'End Date Time' is changed from null to the current date time and the 'End Library Version Number' is changed from null to the current version number. The specific changes to the plurality of version identification values of the library setup snapshot 366 are described below in FIGS. 4, 5, and 7.

A library version under-master snapshot 368 record is updated or generated whenever a corresponding under-master snapshot 354 record is updated or generated, and the applicable infusion master 250 record is referenced by the drug library 260 record. In some implementations, a library version under-master snapshot 368 record is generated for each generated under-master snapshot 354 record and for each drug library 260 record that is referenced by the infusion master 250 record. When a library version under-master snapshot 368 record is updated or created, a plurality of version identification values of the library version under-master snapshot 368 record is updated or populated. In particular, a 'Start Library Version Number,' End Library Version Number,' and 'Initial State Flag' of the plurality of version identification values of the library version under-master snapshot 368 is populated on creation, and just the 'End Library Version Number' is changed on update. The specific changes to the plurality of version identification values of the library version under-master snapshot 368 are described below in FIGS. 4, 5, and 7.

Although not shown, it should be noted that an infusion master 250 record can be associated with zero, one or more external system 270 records.

FIGS. 4-8 illustrates different operations performed by the DLE 220, in accordance with some implementations. The different operations performed by the DLE 220 may be performed at one or more device terminals 32, patient care devices 12, server 30, and/or other device. At least some of the operations performed by the DLE 220 are performed by a computer having a processor executing commands stored in a memory of the computer (e.g., database 37). In some implementations, operations performed by the DLE 220 include retrieving, generating, editing, deleting, and/or storing files in a database that is part of, or is communicably coupled to, a memory (e.g., database 37). In some implementations, information is transmitted between one or more devices in a system (e.g., server 30 and patient care device 12), such as sensor data, stored data, and/or user input information. The operations of the DLE 220 consistent with the present disclosure may include at least some, but not all, of the operations illustrated in FIGS. 4-8, performed in a different sequence. Similarly, one or more operations illustrated in FIGS. 4-8 may be optional. Furthermore, the operations of the DLE 220 consistent with the present disclosure may include at least two or more steps as in FIGS. 4-8 performed overlapping in time, or almost simultaneously.

Figure 4:
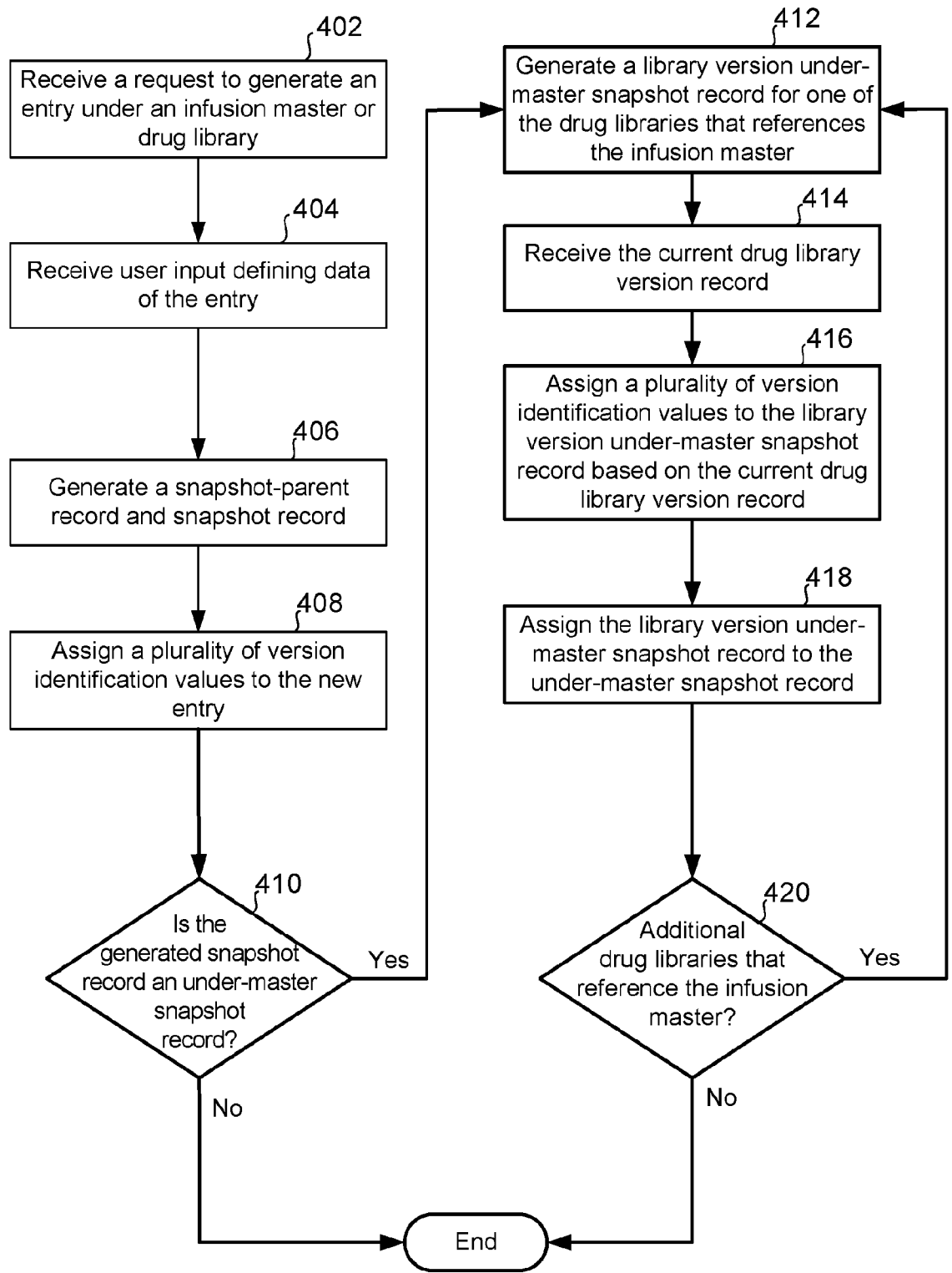
FIG. 4 illustrates a process for the generating entries for an infusion master or drug library, according to various aspects of the subject technology.

FIG. 4 illustrates a process for generating entries under an infusion master 250 or drug library 260, in accordance with some implementations. In some implementations, a request to generate an entry under the infusion master 250 or drug library 260 is received 402 by the DLE 220. An entry, for the purpose of this disclosure, is a combination of a snapshot-parent and a snapshot (non-parent). For example, a user 210 can access the DLE 220 via a device terminal 32 and/or a patient care device 12 and request to generate one or more entries under an infusion master 250 (e.g., under-master snapshot-parent 352 and under-master snapshot 354) or under a drug library 260 (e.g., library setup snapshot-parent 364 and library setup snapshot 366).

The DLE 220 receives 404 user input defining data for the entry. The data provided by the user 210 is used to define one or more parameters (e.g., business data) for the entry under the infusion master 250 or the drug library 260 as described above in reference to FIGS. 3A and 3B. For example, the user 210 can provide data relating to a drug/fluid itself for an under-master snapshot 354 record or data relating to a drug/fluid setup, where the drug/fluid under the infusion master is referenced, for a library setup snapshot 366 record. The DLE 220 generates 406 a snapshot-parent record and a snapshot record when a new entry is generated. For example, if the user provided a request to generate an entry under an infusion master 250, the DLE 220 generates an under-master snapshot-parent 352 record and under-master snapshot 354 record. Alternatively, if the user provided a request to generate an entry under a drug library 260, the DLE 220 generates a library setup snapshot-parent 364 record and library setup snapshot record 366 record.

The DLE 220 assigns 408 a plurality of version identification values to the new entry (on the snapshot record). For instance, for a plurality of version identification values of a library setup snapshot record 366, the DLE 220 assigns a 'Start Date Time' value the current date time, 'End Date Time' value a null value, 'Start Library Version Number' value the value of the library version number currently being edited by the user 210, 'End Library Version Number' value a null value, 'Initial State Flag' value a FALSE value, 'Delete Flag' value a FALSE value, and further links the user identifier value to a user 280 record of the user 210. The DLE 220 assigns the plurality of version identification values to the library setup snapshot 366 record, and further assigns each business attribute to its applicable value as provided by the user 210. For a plurality of version identification values of an under-master snapshot 354 record, the DLE 220 assigns a 'Start Date Time' value the current date time, 'End Date Time' value a null value, 'Delete Flag' value a FALSE value, and further links the user identifier value to the user 280 record of the user 210. The DLE 220 assigns the plurality of version identification values to the under-master snapshot 354 record, and further assigns each business attribute to its applicable value as provided by the user 210. The plurality of version identification values of a respective snapshot record under an infusion master 250 or drug library 260 are not updated after being generated unless the snapshot record is later being superseded by another record and therefore "ended" (End Date Time' set to a non-null value and, if present, 'End Library Version Number' set to a non-null value), when the entry is being changed or logically deleted.

The DLE 220 then determines 410 if a generated snapshot record is an under-master snapshot 354 record. If the generated snapshot record is not an under-master snapshot 354 record, the DLE 220 ends the process. Alternatively, if the generated snapshot record is an under-master snapshot 354 record, the DLE 220 generates 412 a library version under-master snapshot 368 record for one of the drug libraries 260 that references the infusion master 250. The DLE 220 receives 414 the current drug library version 362 record for the drug library 260 and assigns 416 a plurality of version identification values to the library version under-master snapshot 368 record based, in part, on the current drug library version 362 record. In particular, the DLE 220 assigns the plurality of version identification values of the library version under-master snapshot 368 record the following values: a 'Start Library Version Number' value the current library version number for the drug library 260, 'End Library Version Number' value a null value, 'Initial State Flag' value a FALSE value. The DLE 220 further assigns 418 (or links) the library version under-master snapshot 368 record to the new (recently generated) under-master snapshot 354 record.

The DLE 220 determines whether there are any additional drug libraries 260 that reference the infusion master 250 (in which the under-master snapshot 354 record is under). If the DLE 220 determines that there are additional drug libraries 260 that reference the infusion master 250, the DLE 220 performs operations 412 through 418 for each additional drug library 260. If the DLE 220 determines that no additional drug libraries 260 reference the infusion master 250, the DLE 220 ends the process.

Figure 5A:
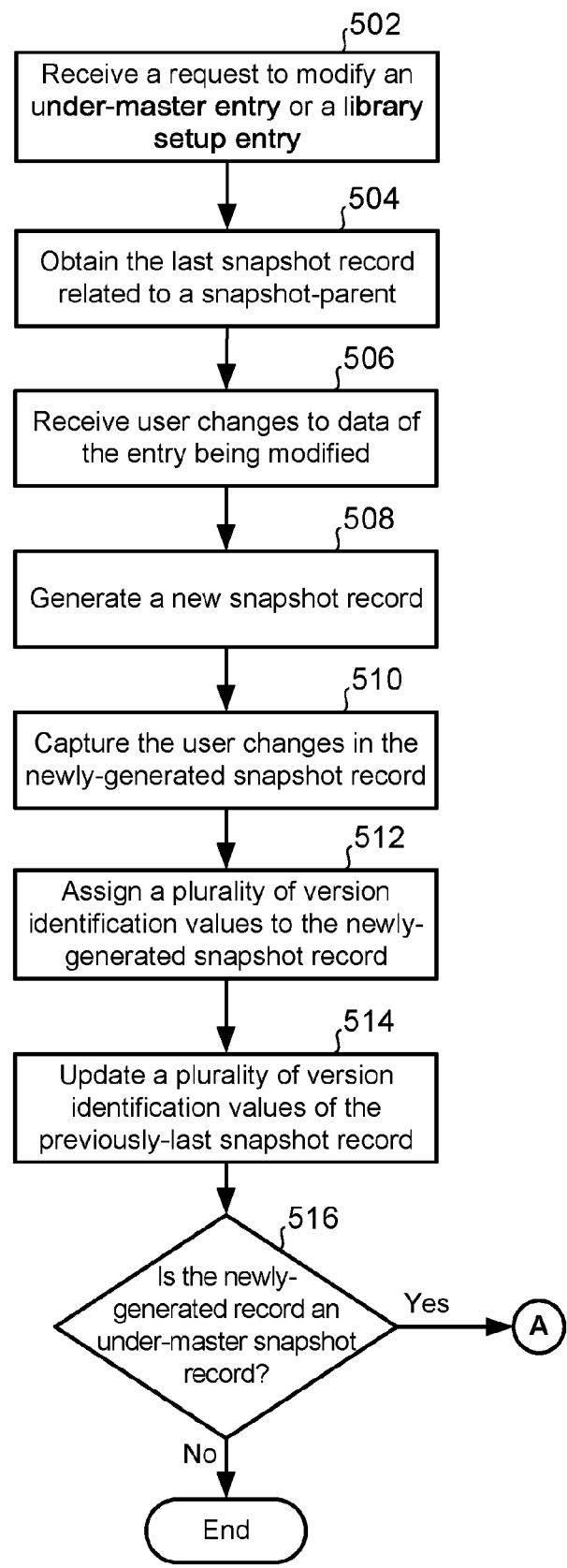
FIGS. 5A and 5B illustrate a process for modifying (including deleting) an entry under an infusion master or drug library, according to various aspects of the subject technology.
Figure 5B:
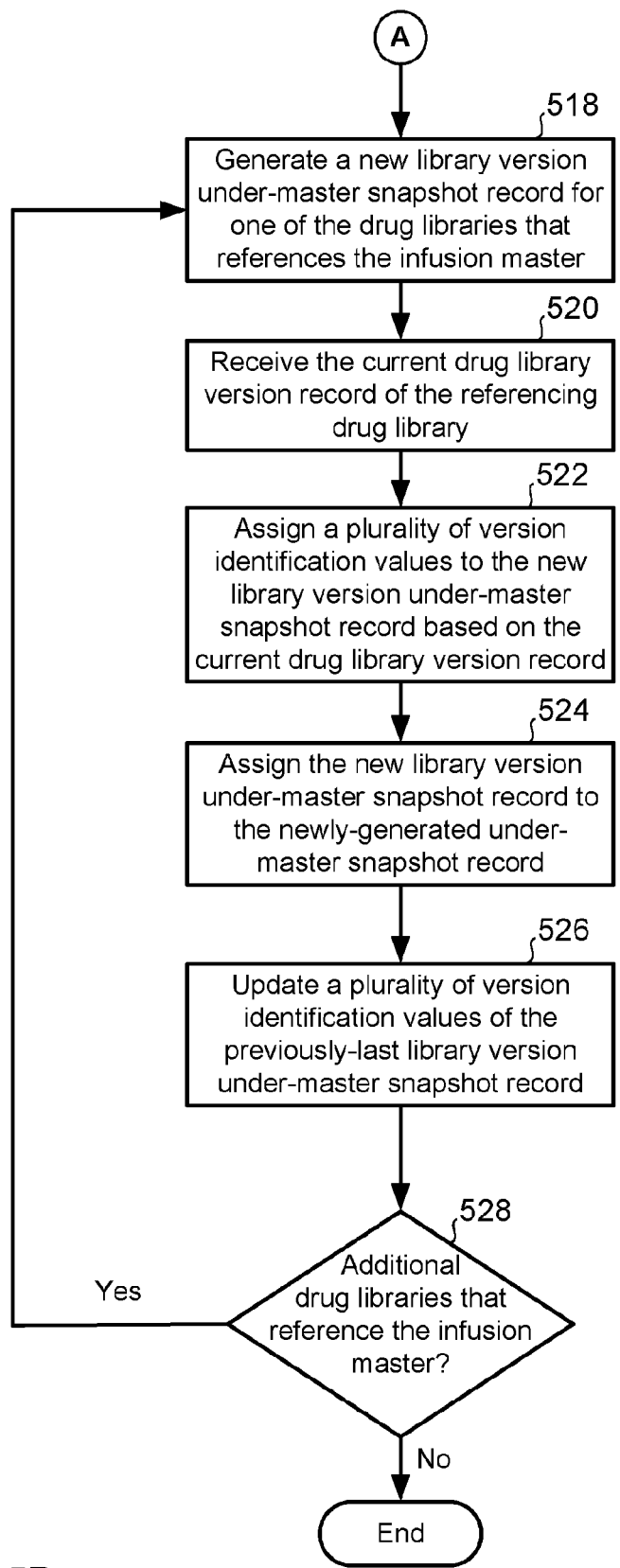

FIGS. 5A and 5B illustrate a process for modifying an entry under an infusion master 250 or drug library 260, in accordance with some implementations. The DLE 220 receives 502 a request from a user 210, via a device terminal 32 or patient care device 12, to modify an under-master snapshot 354 record or library setup snapshot 366 record. In some implementations, modification of an entry includes editing the entry or deleting altogether the entry for an under-master snapshot 354 table or library setup snapshot 366 table. The DLE 220 obtains 504 the last (i.e., where 'End Date Time' is null) snapshot record related to the under-master snapshot-parent 352 record or library setup snapshot-parent 364 record that is being conceptually modified (although note that the snapshot-parent record itself is not modified). The DLE 220 receives 506 user input defining changes to data of the entry being modified, and generates 508 a new snapshot record. For example, a user 210 modifying an under-master entry results in the generation of a new under-master snapshot 354 record. Similarly, the user 210 modifying a library setup entry results in the generation of a new library setup snapshot 366 record.

The DLE 220 captures 510 the user changes to the data in the newly-generated snapshot record, and assigns 512 a plurality of version identification values to the second snapshot record. In particular, the newly-generated snapshot is duplicated from the last snapshot, and used to modify the under-master snapshot 354 table or library setup snapshot record 366 table as requested by the user 210. More specifically, the newly generated under-master snapshot 354 record or library setup snapshot 366 record is used to define one or more parameters (e.g., business data) input by the user. This process is similar to the process for creation of a record under the infusion master 250 or drug library 260 described above in FIG. 4). For instance, for a newly-generated library setup snapshot 366 record, the DLE 220 assigns the following plurality of version identification values: a 'Start Date Time' value the current date time, 'End Date Time' value a null value, 'Start Library Version Number' value the library version number currently being edited by the user 210, 'End Library Version Number' value a null value, 'Initial State Flag' value a FALSE value, 'Delete Flag' value a FALSE value (the value is set to TRUE if the user 210 chose to delete the entry), and further links the user identifier to a user 280 record of the user 210. The DLE 220 further assigns to the newly-generated library setup snapshot 366 record each business attribute to its applicable value assigned by the user 210 (or duplicates the previously-last snapshot record's business data if the entry is deleted by the user 210). For the plurality of version identification values of a newly generated under-master snapshot 354 record the DLE 220 assigns a 'Start Date Time' value the current date time, 'End Date Time' value a null value, 'Delete Flag' value a FALSE value (the value is set to TRUE if the user 210 chose to delete the entry), and further links the user identifier to the user 280 record of the user 210. The DLE 220 further assigns to the newly-generated under-master snapshot 354 record each business attribute to its applicable value assigned by the user 210 (or duplicates the previously-last snapshot record's business-attribute values if the entry is deleted by the user 210).

The DLE 220 also updates 514 a plurality of version identification values of the previously-last snapshot record. In particular, the DLE updates a plurality of version identification values of the immediately preceding under-master snapshot 354 record or immediately preceding library setup snapshot 366 record (depending on the entry that the user 210 requested to modify). For modification to a library setup entry, the DLE 220 assigns the plurality of version identification values of the last library setup snapshot 366 record the following values: 'End Date Time' value the same value as the 'Start Date Time' value of the newly-generated library setup snapshot record 366, and 'End Library Version Number' value the same value as the 'Start Library Version Number' value of the newly-generated library setup snapshot 366 record. For modification to an under-master snapshot 354 record, the DLE 220 assigns the plurality of version identification values of the last under-master snapshot 354 record the following value: 'End Date Time' value the same value as the 'Start Date Time' value of the newly-generated under-master snapshot 354 record.

The DLE 220 determines 516 whether the newly-generated record is an under-master snapshot 354 record. If the newly-generated record is not an under-master snapshot 354 record, the DLE 220 ends the process. Alternatively, if the newly-generated record is an under-master snapshot 354 record, the DLE 220 generates 518 a new library version under-master snapshot 368 record for one of the drug libraries 260 that references (or is linked to) the infusion master 250. For example, if a first drug library 260 record references the infusion master 250 record, the DLE 220 will generate a new library version under-master snapshot 368 record corresponding to the first drug library 260 record. The DLE 220 receives 520 the current drug library version 362 record for the drug library 260 record and assigns 522 a plurality of version identification values to the new library version under-master snapshot 368 record based, in part, on the current drug library version 362 record. The plurality of version identification values to the new library version under-master snapshot 368 record are assigned as described above in operations 412-418 of FIG. 4. The DLE 220 also assigns 524 (or links) the new library version under-master snapshot 368 record to the newly generated under-master snapshot 354 record. The DLE 220 further updates 526 a plurality of version identification values for the last (immediately preceding) library version under-master snapshot 368 record to indicate that a new version is available. More specifically, the DLE 220 updates a plurality of version identification values of the last library version under-master snapshot 368 record with the following value: 'End Library Version Number' value the same value assigned to 'Start Library Version Number' of the new library version under-master snapshot 368 record.

The DLE 220 further determines whether there are any additional drug libraries 260 that reference the infusion master 250 (in which the newly-generated under-master snapshot 354 record is under). If the DLE 220 determines that there are additional drug libraries 260 that reference the infusion master 250, the DLE 220 performs operations 518 through 526 for each additional drug library 260. If the DLE 220 determines that no additional drug libraries 260 reference the infusion master 250, the DLE 220 ends the process.

Figure 6:
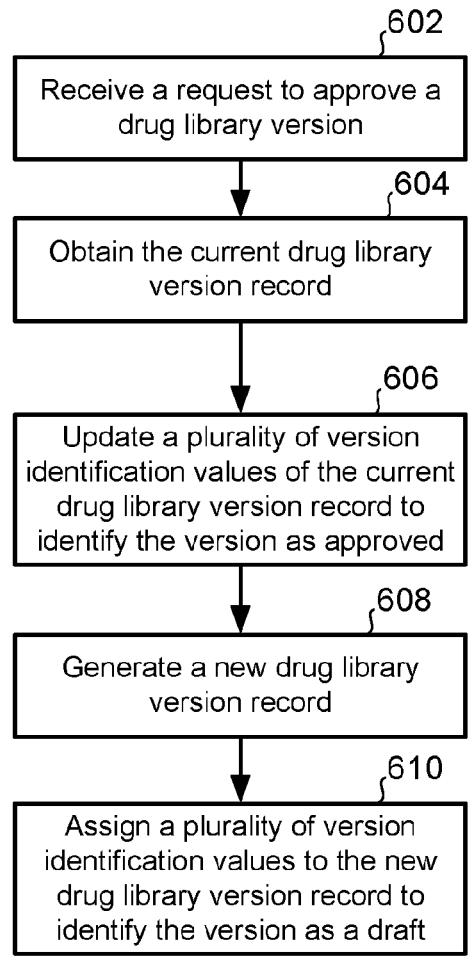
FIG. 6 illustrates a process for approving a draft drug library version, according to various aspects of the subject technology.

FIG. 6 illustrates a process for approving a draft drug library version, in accordance with some implementations. The DLE 220 receives 602 a request to approve a drug library version from the user 210 via a device terminal 32 and/or patient care device 12. The DLE 220 obtains 604 the current drug library version 362 record and updates 606 a plurality of version identification values of the current drug library version 362 record to identify the version as approved. More specifically, the DLE 220 will update a plurality of version identification values of the current drug library version 362 record to change the status of the current drug library version 362 to APPROVED (instead of DRAFT), and set an 'Approval Date Time' value to the current date and time.

The DLE 220 generates 608 a new drug library version 362 record and assigns 610 a plurality of version identification values to the new drug library version 362 record. In particular, the DLE 220 assigns the plurality of version identification values to the new drug library version 362 record such that the new drug library version 362 has a DRAFT status, a 'Library Version Number' value one number greater than the 'Library Version Number' value of the prior drug library version 362 record (i.e., the immediately preceding drug library version 362 record).

Under the rules of the DLE 220, only the new drug library version 362 record for a given drug library 260 is in a DRAFT state. All prior drug library version 362 records (i.e. other than the new drug library version 362 record) for a given library are in an APPROVED state (i.e., drug library version 362 records preceding the most recent drug library version 362 record are in an APPROVED state). Additionally, with respect to the plurality of version identification values on all records under the drug library 260 (i.e., library setup snapshot 366 records) and on all library version under-master snapshot 368 records, the 'End Library Version Number' value (referencing a drug library version 362), if not null, is always greater than or equal to the 'Start Library Version Number' value. When the 'End Library Version Number' value and 'Start Library Version Number' value on the same record are equal to each other, it indicates that the corresponding entry has been modified more than once for a given draft of a drug library version 362. More specifically, each record with a 'Start Library Version Number' and 'End Library Version Number' that are the same is not part of any drug library version 362 that is approved.

FIG. 6 illustrates one approach for approving a drug library version 362, with the new drug library version 362 record being created immediately after the current version is approved. In some other implementations, the DLE 220 waits until some record under a drug library 260 is created or modified (edited or deleted), as described above in FIGS. 4 and 5A-5B, to create a new drug library version 362 in a DRAFT state. When a record under an infusion master 250 is subsequently modified, the current library version number is determined to be one greater than the last approved drug library version 362.

Figure 7A:
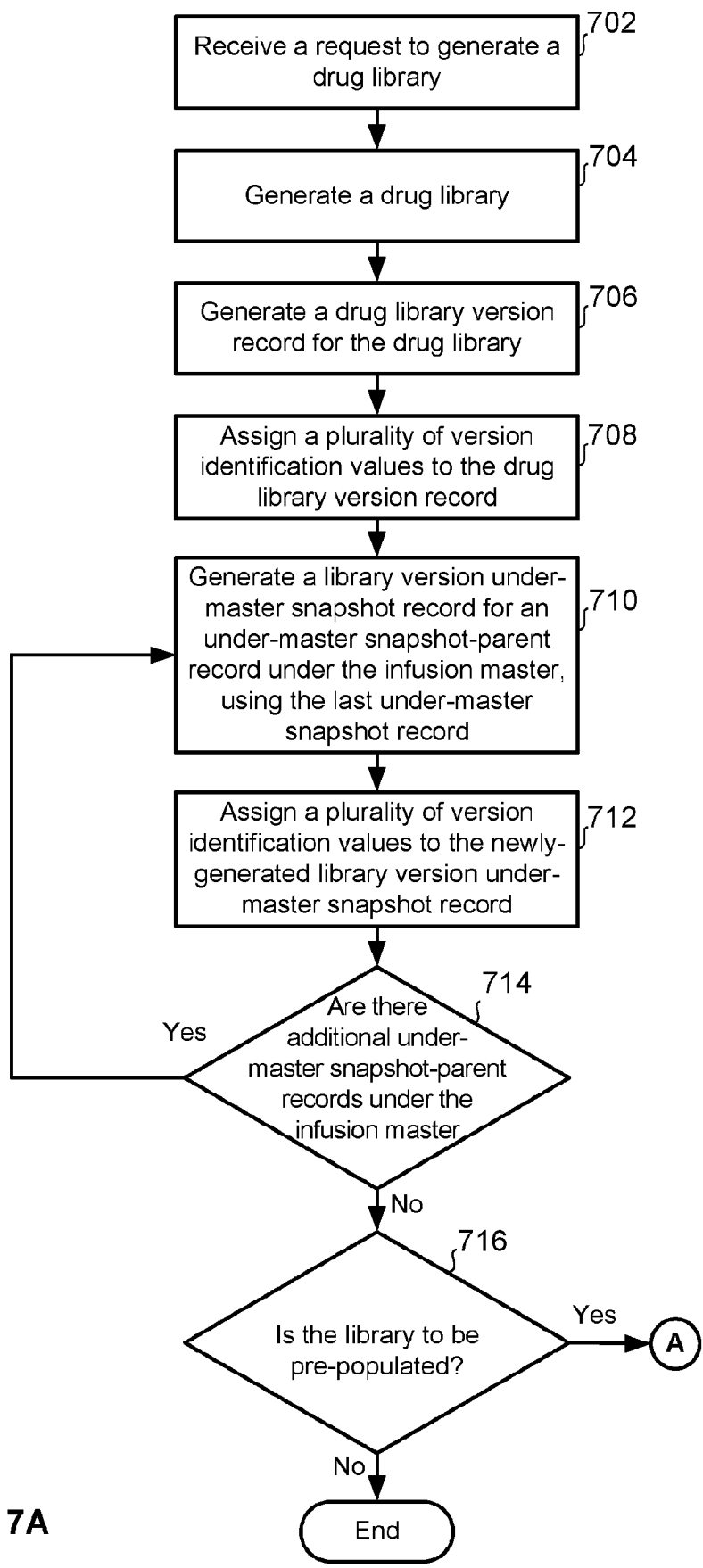
FIGS. 7A and 7B illustrate a process for generating a drug library, according to various aspects of the subject technology.
Figure 7B:
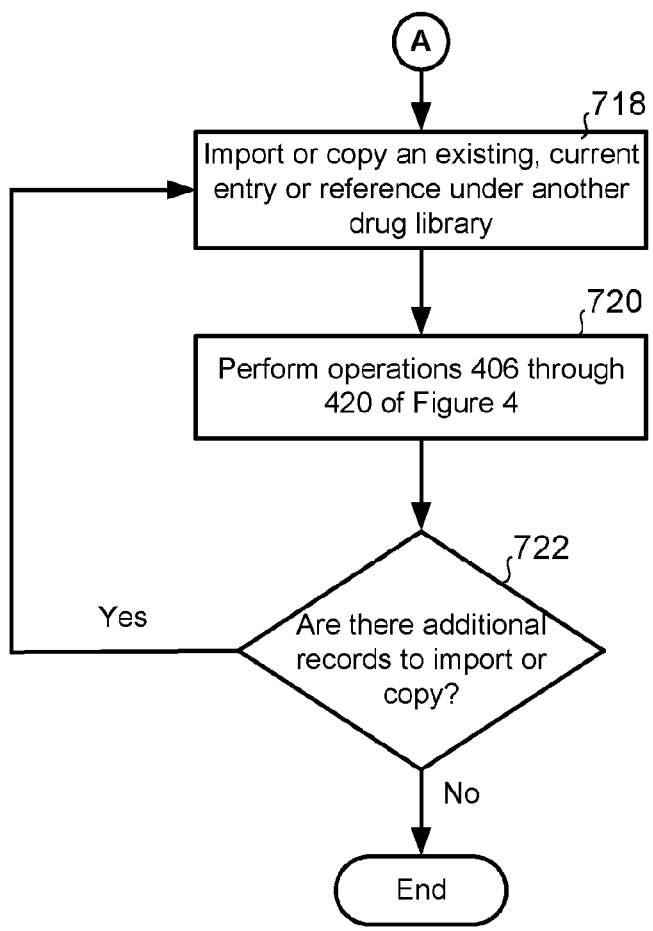

FIGS. 7A and 7B illustrate a process for generating of a drug library 260, in accordance with some implementations. The DLE 220 receives 702 a request to generate a drug library 260 from the user 210 via a device terminal 32 and/or patient care device 12. The DLE 220 generates 704 a drug library 260 record. As mentioned above, the drug library 260 record is linked to a single infusion master 250 record. In some implementations, the user 210 identifies which infusion master 250 record to link the generated drug library 260 record to. The DLE 220 also generates 706 a drug library version 362 record for the new drug library 260 record. The DLE 220 assigns 708 a plurality of version identification values to the new drug library version 362 record. In particular, the DLE 220 assigns the plurality of version identification values of the drug library version 362 record a 'Library Version Number' value of one, and a DRAFT status. In some implementations, the 'Library Version Number' value of the drug library version 362 record is greater than one but does not change the overall process described herein (e.g., the user 210 assigns to the 'Library Version Number' a value greater than 1).

The DLE 220 generates 710 a library version under-master snapshot 368 record for an under-master snapshot-parent 352 record under the infusion master 250 record. The newly-generated library version under-master snapshot 368 record is based on the last (i.e., the latest or current) under-master snapshot 354 record under the infusion master 250. For example, the DLE 220 may generate a first library version under-master snapshot 368 record for a first under-master snapshot 354 record of the infusion master 250 record.

The DLE 220 further assigns 712 a plurality of version identification values to the newly-generated library version under-master snapshot 368 record. In particular, the DLE 220 assigns the plurality of version identification values of the newly-generated library version under-master snapshot 368 record the following values: a 'Start Library Version Number' value the same value as the initial 'Library Version Number' (normally 1), 'End Library Version Number' value a null value, 'Initial State Flag' value a TRUE value. Further, the DLE 220 links the library version under-master snapshot 368 record to an under-master snapshot 354 record, under the infusion master 250, with an 'End Date Time' value of null.

The DLE 220 determines 714 whether there are additional under-master snapshot-parent 352 records under the infusion master 250. If there are additional records under the infusion master 250, the DLE 220 performs operations 710 and 712 for each additional record under the infusion master 250. If there are no additional under-master snapshot-parent 352 records under the infusion master 250, the DLE 220 determines 716 whether the user 210 wants to pre-populate the drug library 260. If the user 210 decides not to pre-populate the drug library 260, the process ends.

Alternatively, if the user 210 decides to pre-populate the drug library 260, the DLE 220 imports or copies 718 an existing, current entry or reference under another drug library 260. For example, the DLE 220 may import or copy (based on the user 210 request) the not-logically-deleted (i.e., the 'Delete Flag' on the current snapshot is FALSE) library setup snapshot-parent 364 and corresponding current library setup snapshot 366 from another drug library 260, distinct from the drug library 260 being generated. As another example, the DLE 220 may import or copy (based on the user 210 request) the not-logically-deleted under-master snapshot-parent 352 record and current under-master snapshot 354 record referenced in another drug library 260, distinct from the drug library 260 being generated. Additionally, the DLE 220 assigns the plurality of version identification values of the library version under-master snapshot 368 record that references the new drug library 260 the following values: a 'Start Library Version Number' value the same value as the initial 'Library Version Number' (typically 1), 'End Library Version Number' value a null value, 'Initial State Flag' value a TRUE value.

The DLE 220 performs 720 operations 406 through 418 of FIG. 4 on the copied or imported existing, current entry or reference under another drug library 260. It should be noted that although the DLE 220 performs similar operations to 406 through 418 of FIG. 4, the plurality of version identification values of the imported existing, current entry or reference under another drug library 260 are distinct for copied or imported records. In particular, the DLE 220 assigns a plurality of version identification values of the copied or imported library setup snapshot 366 the following values: a 'Start Date Time' value the current date time, 'End Date Time' value a null value, 'Start Library Version Number' value the same value as the initial 'Library Version Number' (typically 1), 'End Library Version Number' value a null value, 'Initial State Flag' a TRUE value, and 'Delete Flag' value a FALSE value (because only non-logically deleted records are copied or imported). With respect to a copied or imported under-master snapshot 354 record, the DLE 220 assigns the following plurality of version identification values: a 'Start Date Time' value the current date time, 'End Date Time' value a null value, and 'Delete Flag' value a FALSE value. The DLE 220 further links the copied or imported existing, current entry or reference to the user 210 (i.e., links the user identifier to the user 280 record of the user 210 that created the drug library 260). The DLE 220 also performs operation 420 of FIG. 4, to handle the case where an under-master entry is added and the infusion master 250 is already referenced by one or more pre-existing drug libraries.

The DLE 220 determines 722 whether there are additional records under another drug library 260 that are to be imported or copied. If there are additional records under another drug library 260 that are to be imported or copied, the DLE 220 performs operations 718 and 720 for each additional imported or copied record. If there are no additional records under another drug library 260 that are to be imported or copied, the process ends.

Figure 8:
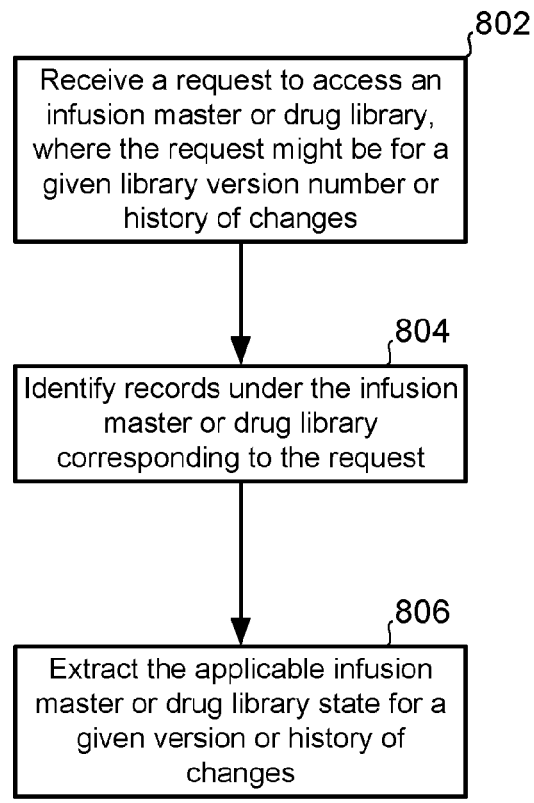
FIG. 8 illustrates a process for querying an infusion master or drug library, according to various aspects of the subject technology.
Figure 9B:
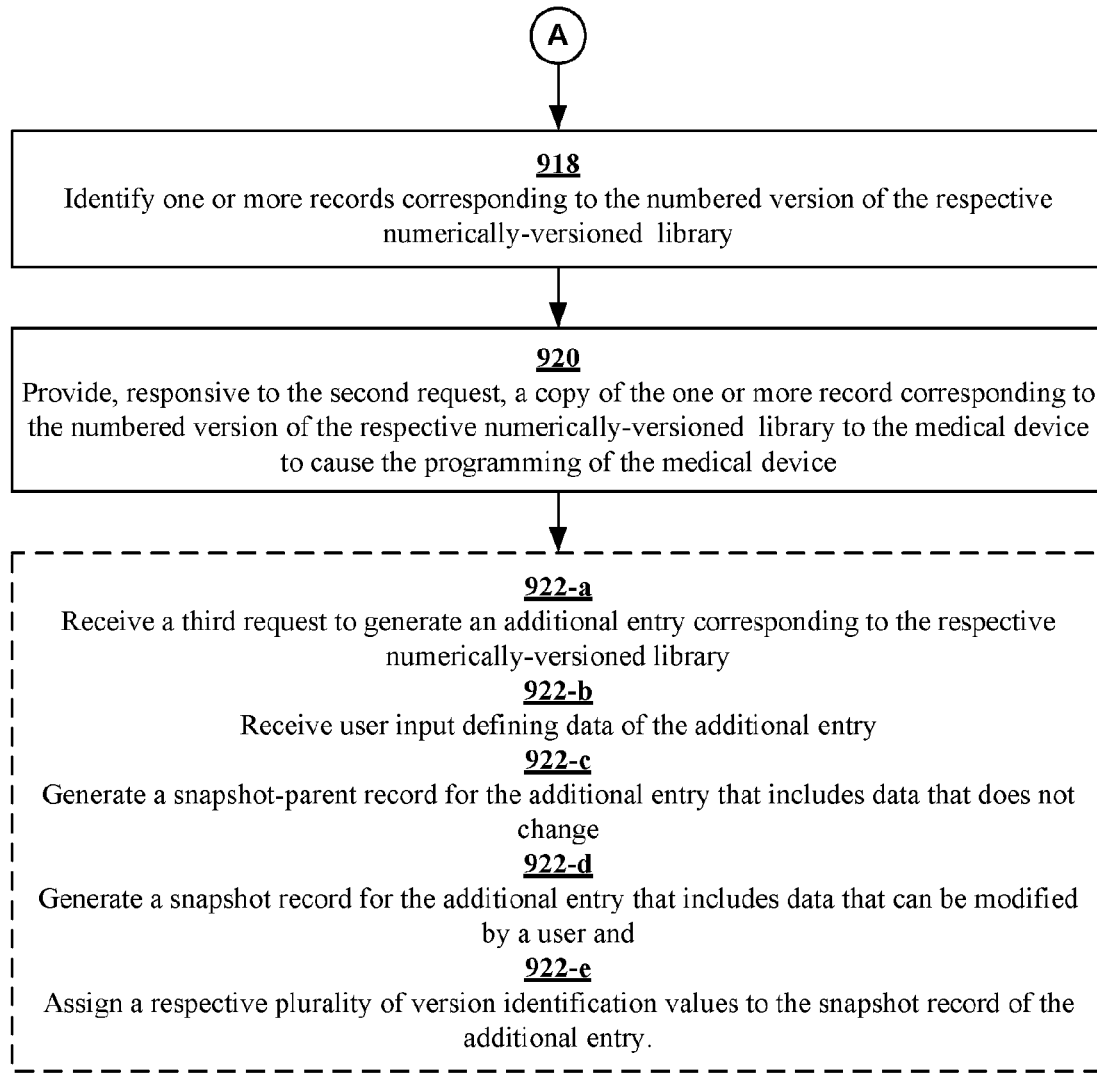
Figure 10A:
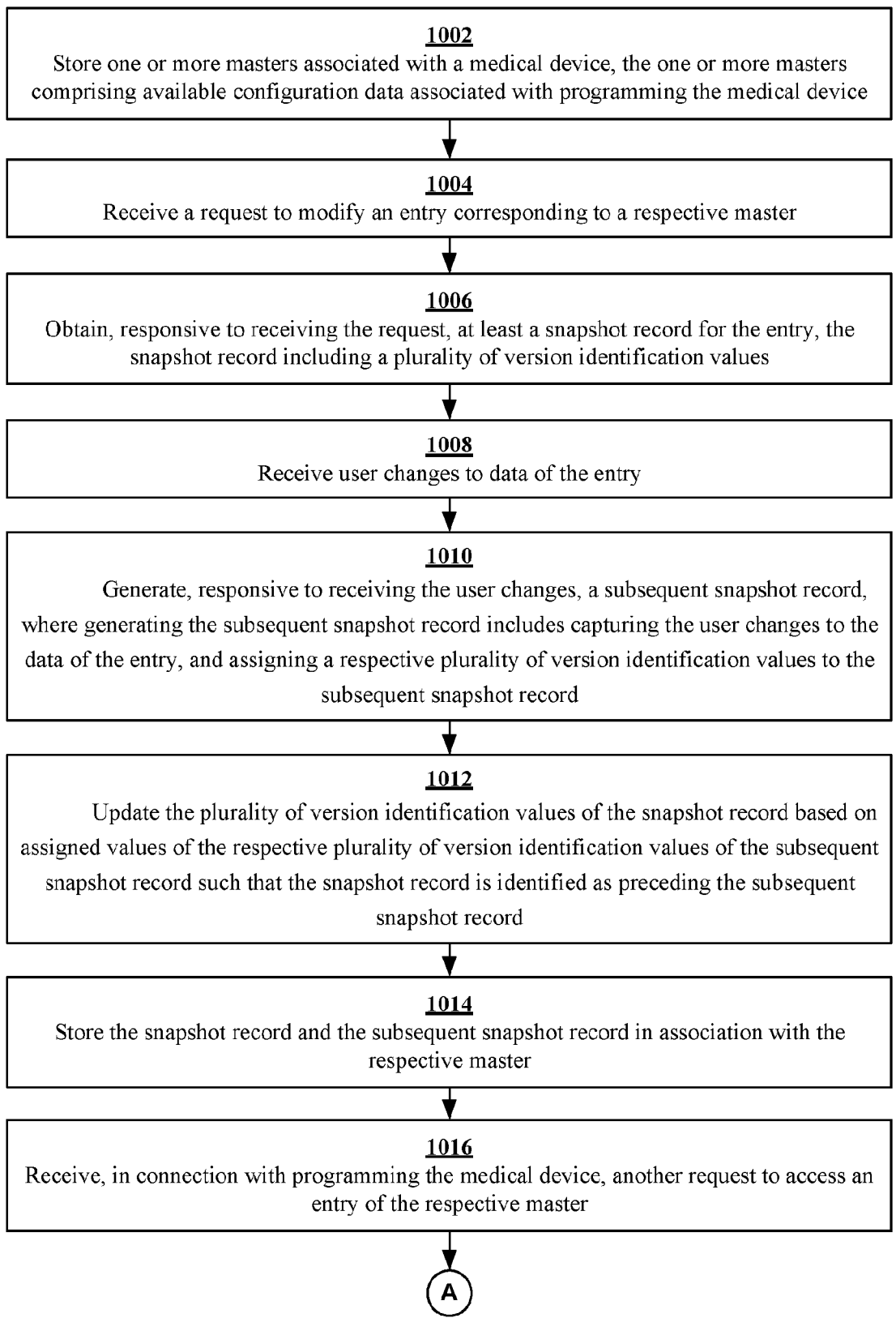
FIGS. 10A-10C are flowcharts illustrating a method for generating or modifying a record under a master, according to various aspects of the subject technology.
Figure 10B:
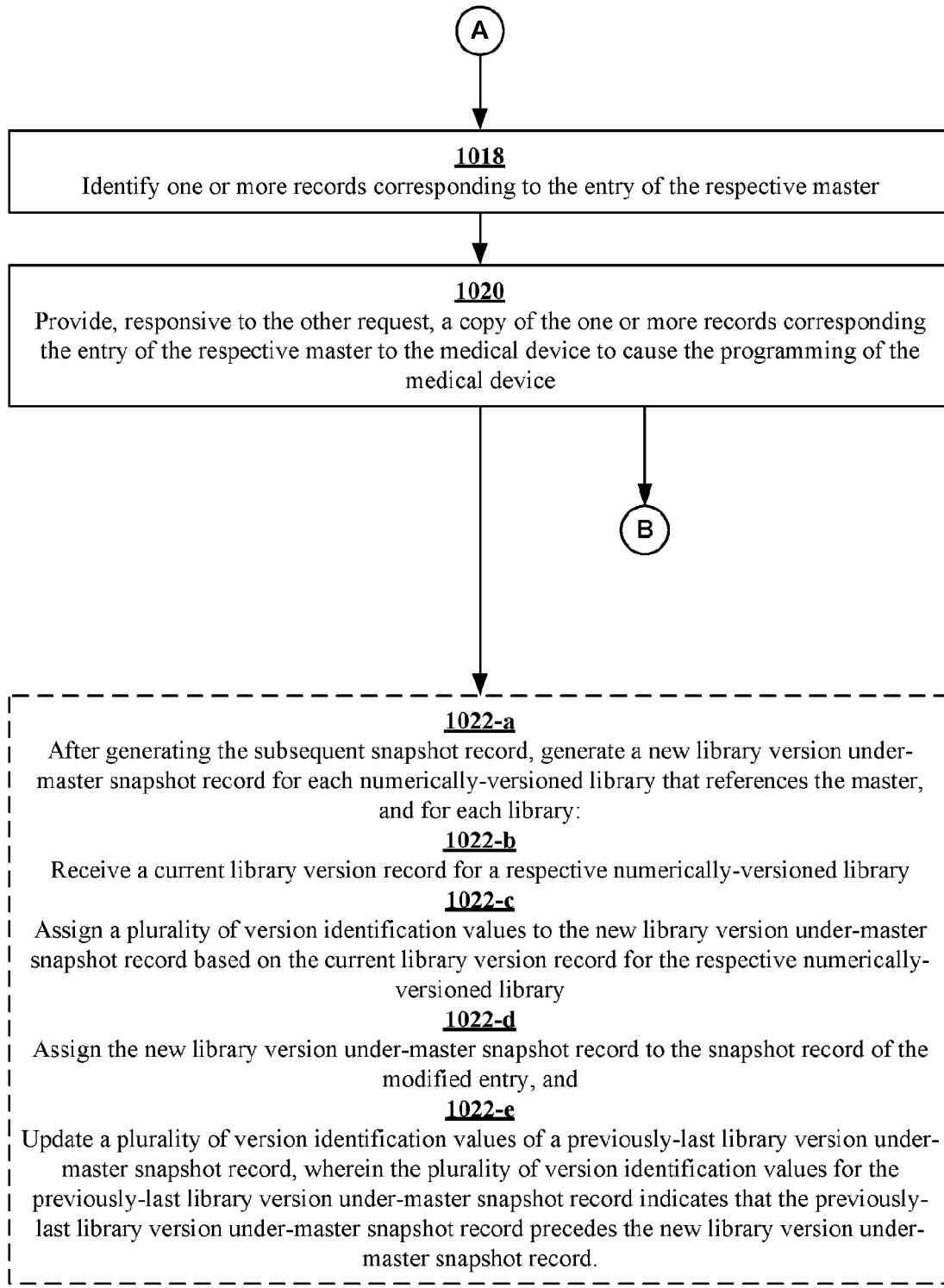
Figure 10C:
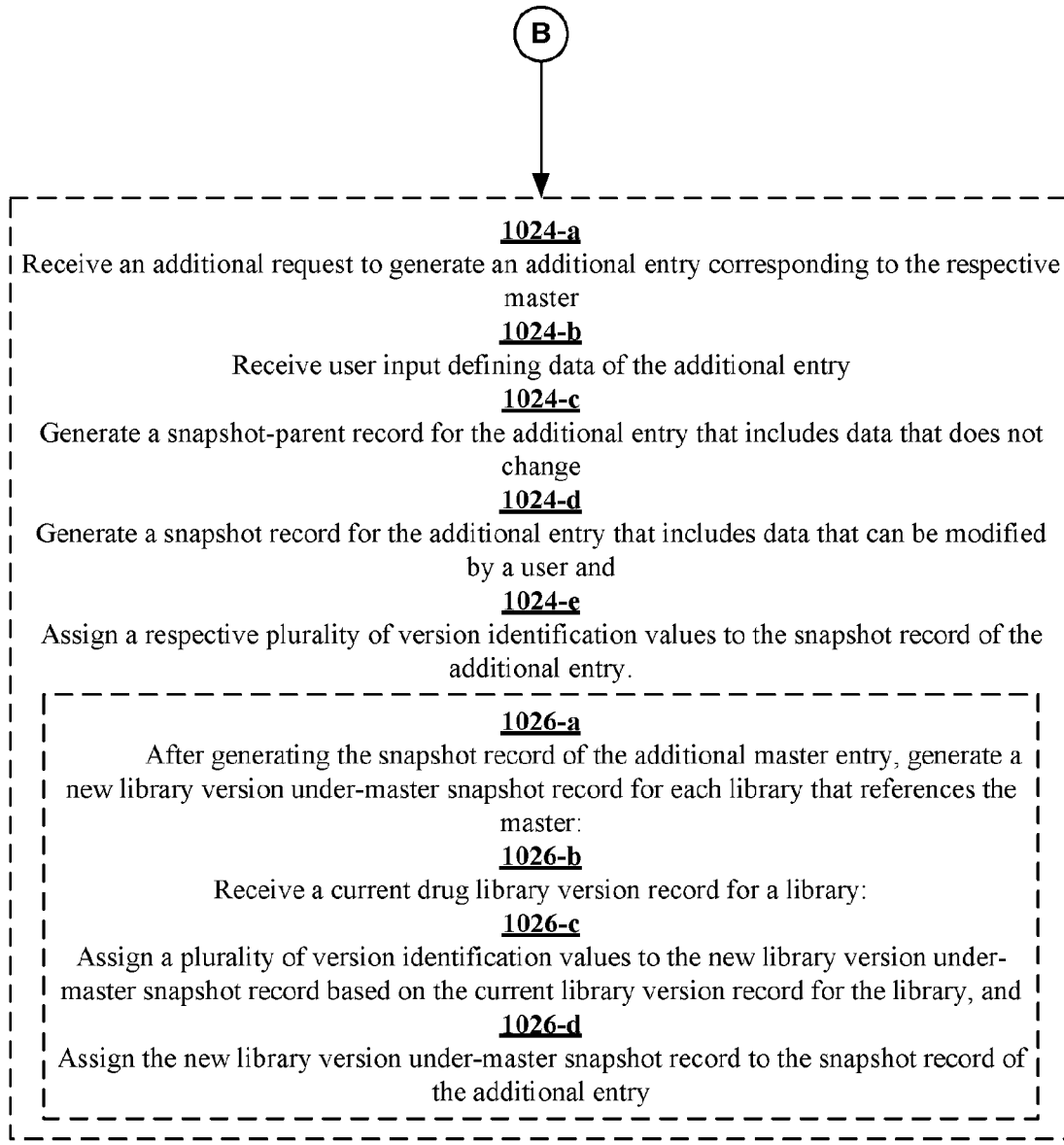

FIG. 8 illustrates a process for querying an infusion master 250 or drug library 260, in accordance with some implementations. In general, a record that includes 'Start Library Version Number' and 'End Library Version Number' applies to "N" version (where N is an integer greater than or equal to 1) where each of the following conditions is satisfied: the 'Start Library Version Number' value is less than or equal to "N," and either the 'End Library Version Number' value is null or greater than "N." For example, a record under a drug library 260 that has a 'Start Library Version Number' of 2 and an 'End Library Version Number' of 6, will be applicable from the 2nd to the 5th versions; however, the record under the drug library 260 would not apply to the 1st version or the 6th version and onwards.

Returning to FIG. 8, the DLE 220 receives 802 a request to access an infusion master 250 or drug library 260 (e.g., via a device terminal 32 or patient care device 12). The request might be for a given library version number or history of changes. The DLE 220 identifies 804 records under the infusion master 250 or drug library 260 corresponding to the request. More specifically, the DLE 220 identifies records under the infusion master 250 or drug library 260 for the applicable version number. For a record under or pertaining to a drug library 260 (e.g., library setup snapshot-parent 364 record and/or library setup snapshot 366 record), the DLE 220 determines whether the following conditions are satisfied: the 'Start Library Version Number' is less than or equal to the version queried (e.g., "N" version), and either the 'End Library Version Number' is null or greater than the version queried. Depending on the nature of the request, whether the 'Delete Flag' is FALSE or TRUE can also be a condition to be satisfied. Further, for a first drug library version 362 that was created via a copy or import (as described above in FIGS. 7A and 7B), the records that have been generated or modified since initial generation must have to have an 'Initial Flag' value equal to FALSE. Alternatively, for a record under an infusion master 250 (e.g., an under-master snapshot-parent 352 record and/or under-master snapshot 354 record), the DLE 220 determines whether the following conditions are satisfied: on its corresponding library version under-master snapshot 368 record that is linked to the queried (or requested) drug library 260 record, the 'Start Library Version Number' value is less than or equal to the version queried (e.g., "N" version), and either the 'End Library Version Number' value is null or greater than the version queried. Depending on the nature of the request, whether the 'Delete Flag' is FALSE or TRUE (on the under-master snapshot 354 record) can also be a condition to be satisfied. Lastly, the under-master snapshot 354 records that have been generated or modified since initial library generation must have to an 'Initial Flag' value on the corresponding library version under-master snapshot 368 record equal to FALSE.

The DLE 220 then extracts 806 the applicable infusion master 250 or drug library 260 state for a given version or history of changes. In this way, DLE 220 allows a user to access and use multiple versions of a drug library 260 without requiring a complete set of files to be copied for each version. More specifically, the different records under the infusion master 250 and/or the different records under the drug library 260 capture complete current and historical data in a highly-efficient manner that can be queried at a later time. Moreover, records can be queried from the perspective of who modified what when, and also from the perspective of how each of the modifications pertain to a particular drug library version. Further, records under an infusion master 250 can be queried from the perspective of how each of the modifications pertain to each applicable drug library version.

FIGS. 9A-9B and 10A-10C are flowcharts illustrating methods for generating or modifying an entry under drug library 260 or infusion master 250, according to some implementations. The methods may be performed at one or more servers 30, device terminals 32, and/or patient care devices 12 via a DLE 220 as discussed above in reference to FIGS. 4-8. Methods consistent with the present disclosure may include at least some, but not all, of the operations illustrated in method 900 and method 1000, performed in a different sequence. Furthermore, methods consistent with the present disclosure may include at least two or more steps as in method 900 and method 1000 performed overlapping in time, or almost simultaneously. For brevity, the different operations of method 900 and method 1000 described below are performed at the server 30 (FIG. 1).

Method 900 includes storing (902) one or more numerically-versioned libraries associated with a medical device, the one or more numerically-versioned libraries comprising available configuration data associated with programming the medical device. In some implementations, a portion of the configuration data is (potentially) shared among one or more numerically-versioned libraries under a related master (e.g., an infusion master 250). Method 900 includes receiving (904) a first request to modify an (existing) entry (e.g., snapshot-parent and snapshot record) corresponding to a respective numerically-versioned library (or a master (e.g., infusion master 250)). In some implementations, the respective numerically-versioned library is a drug library 260 stored in a database 37. The method 900 includes obtaining (906), responsive to receiving the first request, at least a first snapshot record (where the first snapshot record is a previously generated record) for the entry, the first snapshot record including a first plurality of version identification values. The first snapshot record included in the entry is the current, last snapshot record related to a snapshot-parent. For example, in some implementations, the first snapshot record is a current library setup snapshot 366 record under a drug library 260.

The method 900 includes receiving (908) user changes to data of the entry. In particular, a user 210 can request to update portions of or all of the data of the current library setup snapshot 366 record, or delete the entry entirely. The method 900 also includes generating (910), responsive to receiving the user changes, a second snapshot record. Generating the second snapshot record includes capturing the user changes to the data of the entry (along with capturing any modifiable entry data that is not changed (i.e., each snapshot includes all the modifiable data)), and assigning a second plurality of version identification values to the second snapshot record. For example, in some implementations, the second snapshot record is a new library setup snapshot 366 record. Capturing the user changes to the data of the entry include assigning the second snapshot record each business attribute to its applicable value as provided by the user 210. Further, the second plurality of version identification values is used to track a history of the modifications to the entry.

The method 900 includes updating (912) the first plurality of version identification values of the first snapshot record based on assigned values of the second plurality of version identification values of the second snapshot record such that the first snapshot record is identified as preceding the second snapshot record. In this way, the respective pluralities of version identification values are used to track a history of the modifications to the entry. Additional examples of operations (902)-(912) of method 900 are provided above in FIG. 5A.

The method 900 further includes storing (914) the first snapshot record and the second snapshot record in association with the respective numerically-versioned library (or master). For example, a previously-current library setup snapshot record 366 and a new library setup snapshot record 366 are stored in association with their corresponding drug library 260. The method 900 includes receiving (916), in connection with programming the medical device, a second request to access a numbered version of the respective library, and identifying (918) one or more records corresponding to the numbered version of the respective numerically-versioned library. For example, a user 210 may request, via the DLE 220, to configure a medical device (e.g., a patient care device 12) in accordance with a particular numbered version of a drug library 260, including the applicable state of the related infusion master 250, and the DLE 220 identifies the applicable records corresponding to the user's request. The method 900 further includes providing (920), responsive to the second request, a copy of the one or more record corresponding to the numbered version of the respective numerically-versioned library to the medical device to cause the programming of the medical device. Additional examples of operations (916)-(920) of method 900 are provided above in FIG. 8.

In some implementations, the method 900 includes receiving (922-a) a third request to generate an additional entry corresponding to the respective numerically-versioned library. For example, an entry under a drug library 260. The method 900 includes receiving (922-b) user input defining data of the additional entry, and generating (922-c) a snapshot-parent record for the additional entry that includes data that does not change; and generating (922-d) a snapshot record for the additional entry that includes data that can be modified by a user. The method further includes assigning (924-e) a respective plurality of version identification values to the snapshot record of the additional entry. Additional examples of operations (922-a)— (922-e) of method 900 are provided above in FIG. 4.

Method 1000 includes storing (1002) one or more masters (e.g., infusion masters 250) associated with a medical device, the one or more masters comprising available configuration data associated with programming the medical device. Method 1000 includes receiving (1004) a request to modify an (existing) entry (e.g., snapshot-parent and snapshot record) corresponding to a respective master. In some implementations, the respective master is an infusion master 250 stored in a database 37. The method 1000 includes obtaining (1006), responsive to receiving the request, at least a snapshot record (where the snapshot record is a previously generated record) for the entry, the snapshot record including a plurality of version identification values. The snapshot record included in the entry is the current, last snapshot record related to a snapshot-parent. For example, in some implementations, the snapshot record is the current under-master snapshot 354 under an infusion master 250.

The method 1000 includes receiving (1008) user changes to data of the entry. In particular, a user 210 can request to update portions of or all of the data of the current under-master snapshot record, or delete the entry entirely. The method 1000 also includes generating (1010), responsive to receiving the user changes, a subsequent snapshot record. Generating the subsequent snapshot record includes capturing the user changes to the data of the entry (along with capturing any modifiable entry data that is not changed (i.e., each snapshot includes all the modifiable data)), and assigning a respective plurality of version identification values to the subsequent snapshot record. For example, in some implementations, the subsequent snapshot record is a new under-master snapshot 354 record. Capturing the user changes to the data of the entry include assigning the subsequent snapshot record each business attribute to its applicable value as provided by the user 210. Further, the respective plurality of version identification values is used to track a history of the modifications to the entry.

The method 1000 includes updating (1012) the plurality of version identification values of the snapshot record based on assigned values of the respective plurality of version identification values of the subsequent snapshot record such that the snapshot record is identified as preceding the subsequent snapshot record. In this way, the respective pluralities of version identification values are used to track a history of the modifications to the entry. Additional examples of operations (1002)-(1012) of method 1000 are provided above in FIG. 5A.

The method 1000 further includes storing (1014) the snapshot record and the subsequent snapshot record in association with the respective master. For example, a current under-master snapshot 354 record and a new under-master snapshot 354 record are stored in association with their corresponding infusion master 250. The method 1000 includes receiving (1016), in connection with programming the medical device, another request to access an entry of the respective master, and identifying (1018) one or more records corresponding to the entry of the respective master. For example, a user 210 may request, via the DLE 220, to configure a medical device (e.g., a patient care device 12) in accordance with a particular entry of an infusion master 250, including a particular numbered version of a drug library 260 related to the infusion master 250, and the DLE 220 identifies the applicable records corresponding to the user's request. The method 1000 further includes providing (1020), responsive to the other request, a copy of the one or more records corresponding to the entry of the respective master to the medical device to cause the programming of the medical device. Additional examples of operations (1016)-(1020) of method 1000 are provided above in FIG. 8.

In some implementations, the method 1000 includes, after generating the subsequent snapshot record, generating (1022-a) a new library version under-master snapshot record for each library that references the master. Further, for each library that references the master, the method includes receiving (1022-b) a current library version record for a library, assigning (1022-c) a plurality of version identification values to the new library version under-master snapshot record based on the current library version record for the library, and assigning (1022-d) the new library version under-master snapshot record to the subsequent snapshot record of the modified entry. The method 1000 further includes, for each library, updating (1022-e) a plurality of version identification values of a previously-last library version under-master snapshot record, the plurality of version identification values for the previously-last library version under-master snapshot record indicating that the previously-last library version under-master snapshot record precedes the new library version under-master snapshot record. Additional examples of operations (1022-a)-(1022-e) of method 1000 are provided above in reference to FIG. 5B.

In some implementations, the method 1000 includes receiving (1024-a) an additional request to generate an additional entry corresponding to the respective master. For example, an entry under an infusion master 250. The method 1000 includes receiving (1024-b) user input defining data of the additional entry, and generating (1024-c) a snapshot-parent record for the additional entry that includes data that does not change; and generating (1024-d) a snapshot record for the additional entry that includes data that can be modified by a user. The method further includes assigning (1024-e) a respective plurality of version identification values to the snapshot record of the additional entry. Additional examples of operations (1024-a)-(1024-e) of method 1000 are provided above in FIG. 4.

In some implementations, after generating the snapshot record of the additional master entry, the method 1000 includes generating (1026-a) a new library version under-master snapshot record for each library that references the master. Further, for each library that references the master, the method 1000 includes receiving (1026-b) a current library version record for a library, assigning (1026-c) a plurality of version identification values to the new library version under-master snapshot record based on the current library version record for the library, and assigning (1026-d) the new library version under-master snapshot record to the snapshot record of the additional entry. Additional examples of operations (1026-a)-(1026-d) of method 1000 are provided above in FIG. 4.

Figure 11:
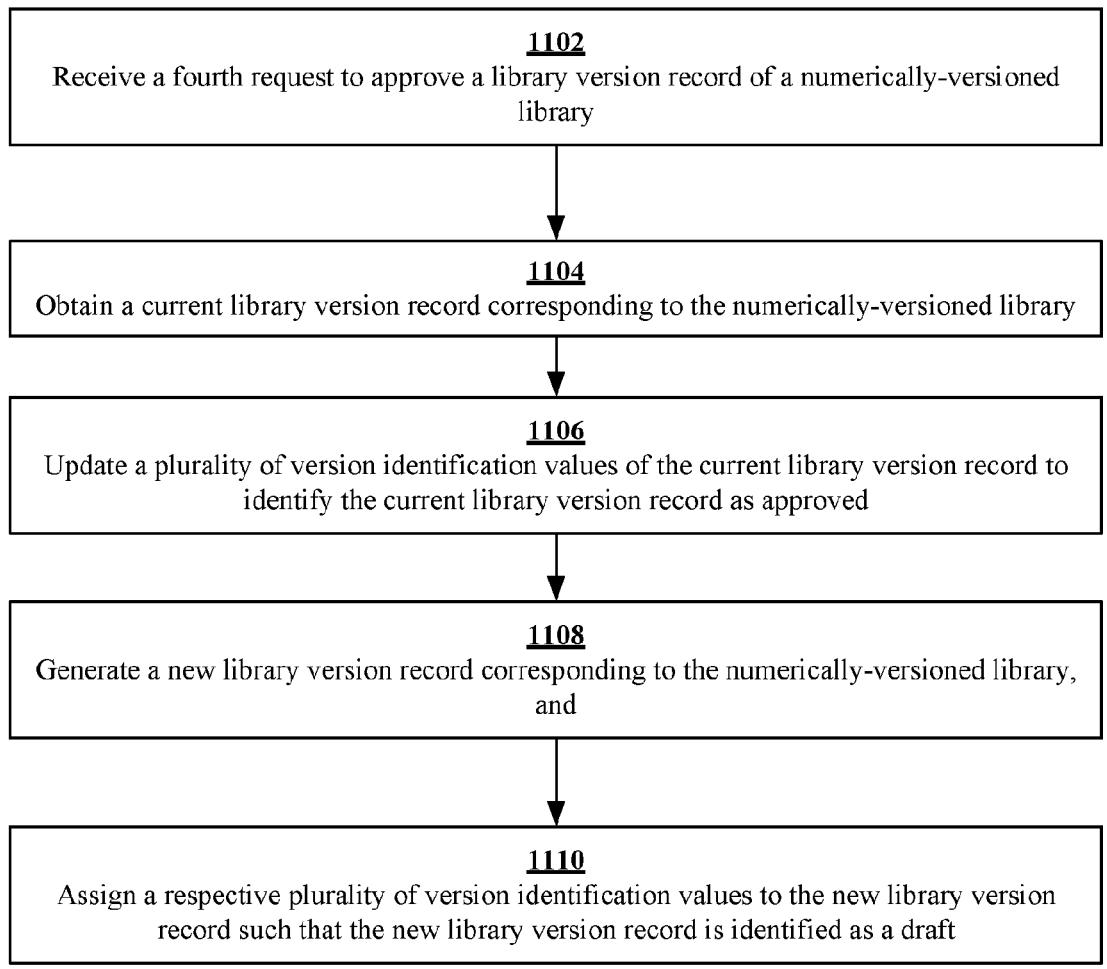
FIG. 11 is a flowchart illustrating a method for approving a version of a numerically-versioned library, according to various aspects of the subject technology.

FIG. 11 is a flowchart illustrating a method 1100 for approving a library version according to some implementations. Method 1100 may be performed at one or more servers 30, device terminals 32, and/or patient care devices 12 via a DLE 220 as discussed above in reference to FIGS. 4-9. Methods consistent with the present disclosure may include at least some, but not all, of the operations illustrated in method 1100, performed in a different sequence. Furthermore, methods consistent with the present disclosure may include at least two or more steps as in method performed overlapping in time, or almost simultaneously. For brevity, the different operations of method 1100 described below are performed at the server 30 (FIG. 1).

Method 1100 includes receiving (1102) a fourth request to approve a library version record of a library. The method 1100 includes obtaining (1104) a current library version record corresponding to the library, and updating (1106) a plurality of version identification values of the current library version record to identify the current library version record as approved. The method 1100 further includes generating (1108) a new library version record corresponding to the library, and assigning (1110) a respective plurality of version identification values to the new library version record such that the new library version record is identified as a draft. Additional examples of operations 1102-1110 of method 1100 are provided above in FIG. 6.

Figure 12:
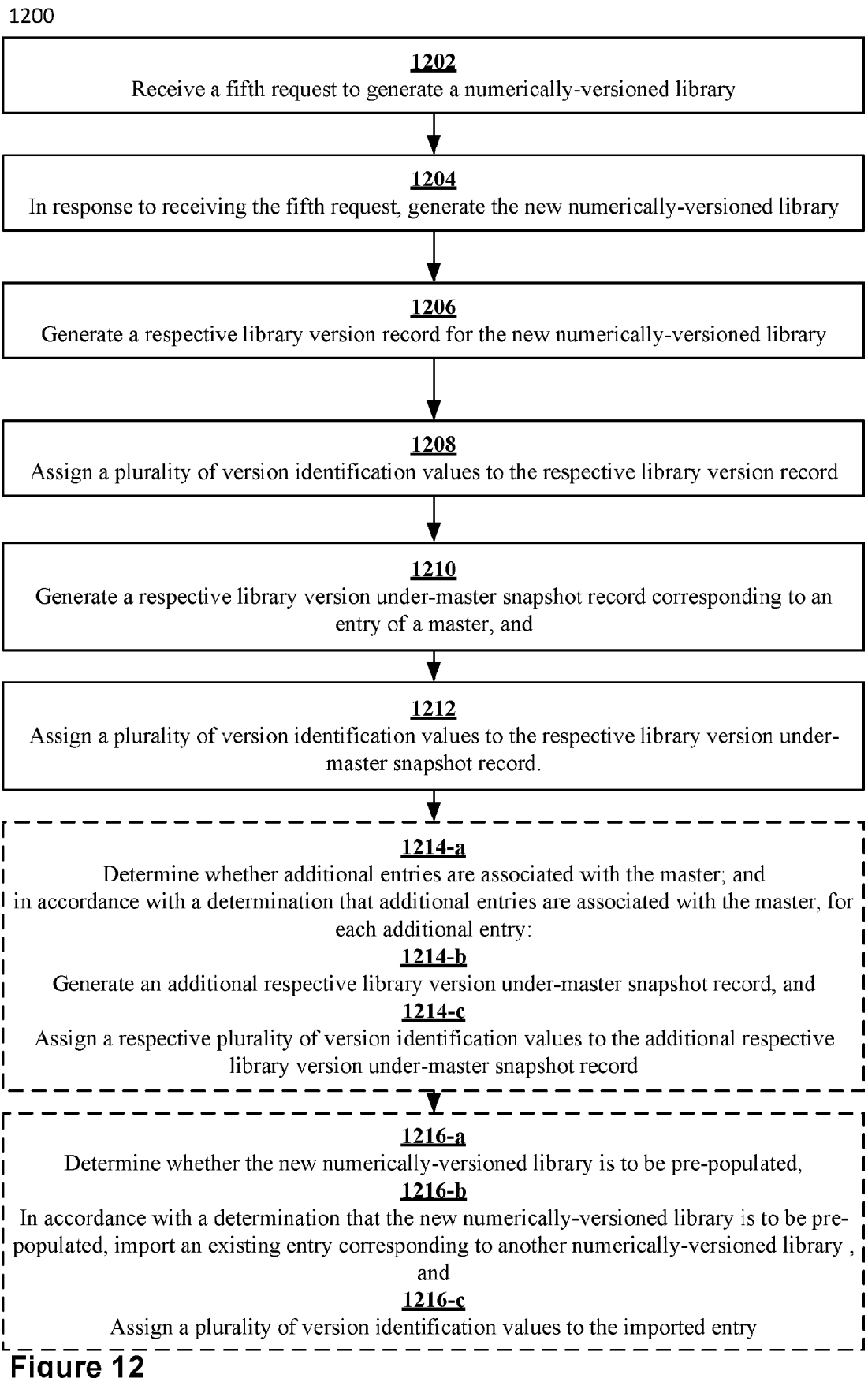
FIG. 12 is a flowchart illustrating a method for generating a numerically-versioned library, according to various aspects of the subject technology.

FIG. 12 is a flowchart illustrating a method 1200 for generating a library according to some implementations. Method 1200 may be performed at one or more servers 30, device terminals 32 and/or patient care devices 12 via a DLE 220 as discussed above in reference to FIGS. 4-10. Methods consistent with the present disclosure may include at least some, but not all, of the operations illustrated in method 1200, performed in a different sequence. Furthermore, methods consistent with the present disclosure may include at least two or more steps as in method performed overlapping in time, or almost simultaneously. For brevity, the different operations of method 1200 described below are performed at the server 30 (FIG. 1).

Method 1200 includes receiving (1202) a fifth request to generate a library, and, in response to receiving the fifth request, generating (1204) the new library. The method 1200 further includes generating (1206) a respective library version record for the new library and assigning (1208) a plurality of version identification values to the respective library version record. The method 1200 includes generating (1210) a respective library version under-master snapshot record corresponding to an entry of a master referenced by the library, and assigning (1212) a plurality of version identification values to the respective library version under-master snapshot record. In some implementations, method 1200 further includes determining (1214-a) whether additional entries are associated with the master, and in accordance with a determination that additional entries are associated with the master, for each additional entry: generating (1214-b) an additional respective library version under-master snapshot record, and assigning (1214-c) a respective plurality of version identification values to the additional respective library version under-master snapshot record. In some implementations, method 1200 includes determining (1216-a) whether the library is to be pre-populated, and in accordance with a determination that the library is to be pre-populated, importing (1216-b) an existing entry corresponding to another library, and assigning (1216-c) a plurality of version identification values to the imported entry. Additional examples of operations 1202-1216 of method 1200 are provided above in FIGS. 7A and 7B.

Figure 13:
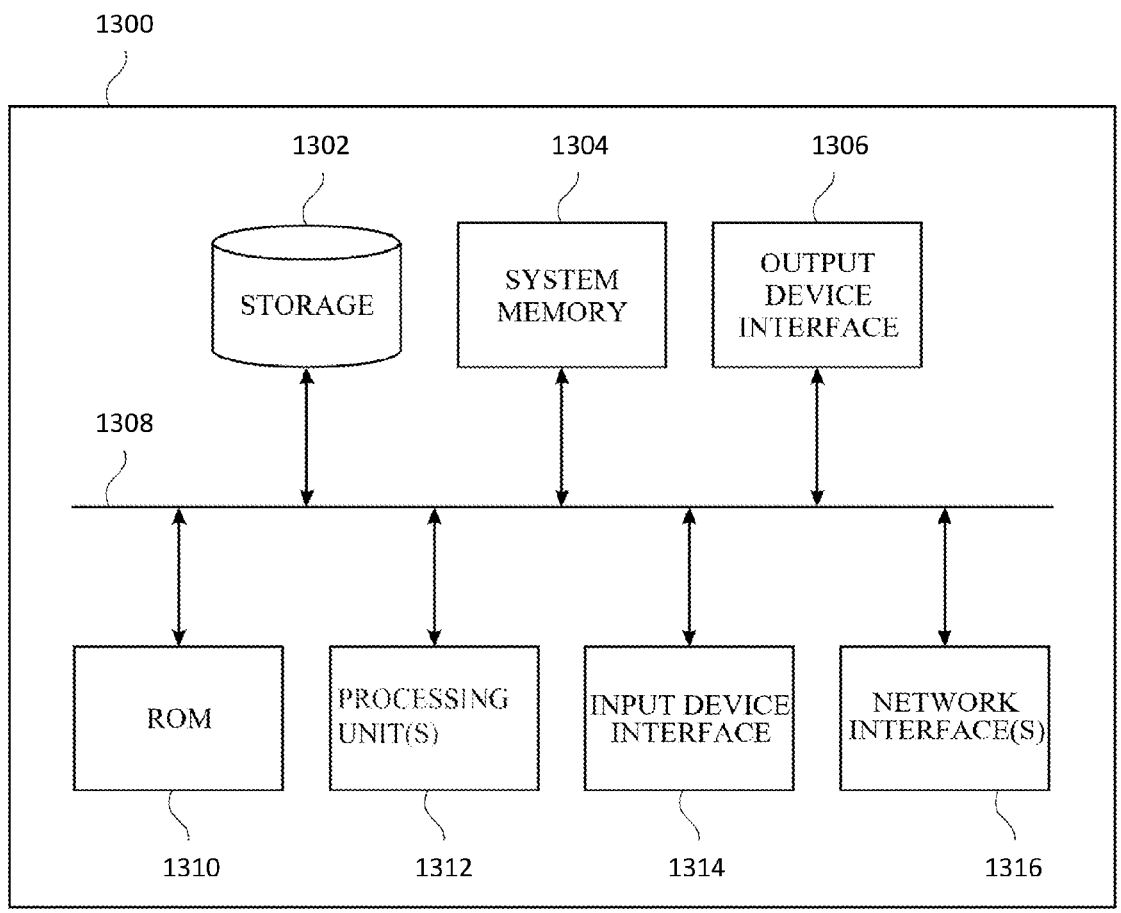
FIG. 13 is a conceptual diagram illustrating an example electronic system for implementing a drug library editor, according to various aspects of the subject technology.

FIG. 13 is a conceptual diagram illustrating an example electronic system 1300 for implementing a DLE 220, according to various aspects of the subject technology. Electronic system 1300 may be a computing device for execution of software associated with one or more portions or steps of processes 900, 1000, 1100, and/or 1200; or components and processes provided by FIGS. 1-12. Electronic system 1300 may be representative, in combination with the disclosure regarding FIGS. 1-12, of the DLE 220 described above. In this regard, electronic system 1300 may be a microcomputer, personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 1300 may include various types of computer readable media and interfaces for various other types of computer readable media. In the depicted example, electronic system 1300 includes a bus 1308, processing unit(s) 1312, a system memory 1304, a read-only memory (ROM) 1310, a permanent storage device 1302, an input device interface 1314, an output device interface 1306, and one or more network interfaces 1316. In some implementations, electronic system 1300 may include or be integrated with other computing devices or circuitry for operation of the various components and processes previously described.

Bus 1308 collectively represents all system, peripheral, and chipset buses that communicatively connect the numerous internal devices of electronic system 1300. For instance, bus 1308 communicatively connects processing unit(s) 1312 with ROM 1310, system memory 1304, and permanent storage device 1302.

From these various memory units, processing unit(s) 1312 retrieves instructions to execute and data to process in order to execute the processes of the subject disclosure. The processing unit(s) can be a single processor or a multi-core processor in different implementations.

ROM 1310 stores static data and instructions that are needed by processing unit(s) and other modules of the electronic system. Permanent storage device 1302, on the other hand, is a read-and-write memory device. This device is a non-volatile memory unit that stores instructions and data even when electronic system 1300 is off. Some implementations of the subject disclosure use a mass-storage device (such as a magnetic or optical disk and its corresponding disk drive) as permanent storage device 1302.

Some implementations use a removable storage device (such as a floppy disk, flash drive, and its corresponding disk drive) as permanent storage device 1302. Like permanent storage device 1302, system memory 1304 is a read-and-write memory device. However, unlike storage device 1302, system memory 1304 is a volatile read-and-write memory, such a random access memory. System memory 1304 stores some of the instructions and data that the processor needs at runtime. In some implementations, the processes of the subject disclosure are stored in system memory 1304, permanent storage device 1302, and/or ROM 1310. From these various memory units, processing unit(s) 1312 retrieves instructions to execute and data to process in order to execute the processes of some implementations.

Bus 1308 also connects to input and output device interfaces 1314 and 1306. Input device interface 1314 enables the user to communicate information and select commands to the electronic system. Input devices used with input device interface 1314 include, e.g., alphanumeric keyboards and pointing devices (also called "cursor control devices"). Output device interfaces enables, e.g., the display of images generated by the electronic system 1300. Output devices used with output device interface 1306 include, e.g., printers and display devices, such as cathode ray tubes (CRT) or liquid crystal displays (LCD). Some implementations include devices such as a touchscreen that functions as both input and output devices.

Also, bus 1308 also couples electronic system 1300 to a network (not shown) through network interfaces 1316. Network interfaces 1316 may include, e.g., a wireless access point (e.g., Bluetooth or WiFi) or radio circuitry for connecting to a wireless access point. Network interfaces 1316 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 1300 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Aspects described include artificial intelligence or other operations whereby the system processes inputs and generates outputs with apparent intelligence. The artificial intelligence may be implemented in whole or in part by a model. A model may be implemented as a machine learning model. The learning may be supervised, unsupervised, reinforced, or a hybrid learning whereby multiple learning techniques are employed to generate the model. The learning may be performed as part of training. Training the model may include obtaining a set of training data and adjusting characteristics of the model to obtain a desired model output. For example, three characteristics may be associated with a desired item location. In such instance, the training may include receiving the three characteristics as inputs to the model and adjusting the characteristics of the model such that for each set of three characteristics, the output device state matches the desired device state associated with the historical data.

In some implementations, the training may be dynamic. For example, the system may update the model using a set of events. The detectable properties from the events may be used to adjust the model.

The model may be an equation, artificial neural network, recurrent neural network, convolutional neural network, decision tree, or other machine-readable artificial intelligence structure. The characteristics of the structure available for adjusting during training may vary based on the model selected. For example, if a neural network is the selected model, characteristics may include input elements, network layers, node density, node activation thresholds, weights between nodes, input or output value weights, or the like. If the model is implemented as an equation (e.g., regression), the characteristics may include weights for the input parameters, thresholds or limits for evaluating an output value, or criterion for selecting from a set of equations.

Once a model is trained, retraining may be included to refine or update the model to reflect additional data or specific operational conditions. The retraining may be based on one or more signals detected by a device described herein or as part of a method described herein. Upon detection of the designated signals, the system may activate a training process to adjust the model as described.

Further examples of machine learning and modeling features which may be included in the embodiments discussed above are described in "A survey of machine learning for big data processing" by Qiu et al. in EURASIP Journal on Advances in Signal Processing (2016).

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A method of managing one or more records for a medical device, comprising:

storing one or more numerically-versioned libraries associated with a medical device at an external database, the one or more numerically-versioned libraries comprising configuration data associated with programming the medical device;

receiving a first request to modify an entry corresponding to a respective numerically-versioned library;

obtaining, responsive to receiving the first request, at least a first snapshot record for the entry, the first snapshot record including a first plurality of version identification values and a first data structure including a first version history such that a copy of the first snapshot is not created to change the respective numerically-versioned library;

receiving user changes to data of the entry;

generating, responsive to receiving the user changes, a second snapshot record for the entry that includes a second data structure including a second version history such that a copy of the second snapshot is not created to change the respective numerically-versioned library, wherein generating the second snapshot record includes:
  capturing the user changes to the data of the entry, and assigning a second plurality of version identification values to the second snapshot record;
updating the first plurality of version identification values of the first snapshot record based on assigned values of the second plurality of version identification values of the second snapshot record such that the first snapshot record is identified as preceding the second snapshot record;
storing the first snapshot record and the second snapshot record in association with the respective numerically-versioned library at the external database such that duplicate entries are not generated;
receiving, in connection with programming the medical device, a second request to access a numbered version of the respective numerically-versioned library from the external database;
identifying one or more records corresponding to the numbered version of the respective numerically-versioned library; and
providing, responsive to the second request, a copy of the one or more record corresponding to the numbered version of the respective numerically-versioned library from the external database to the medical device to cause the programming of the medical device.

2. The method of claim 1, wherein updating the first plurality of version identification values of the first snapshot record based on assigned values of the second plurality of version identification values of the second snapshot includes:
  assigning a start value of the second plurality of version identification values of the second snapshot record as an end value for first plurality of version identification values of the first snapshot record.

3. The method of claim 1, wherein the second plurality of version identification values include one or more of a start date, end date, start library version number, and end library version number.

4. The method of claim 1, wherein the second plurality of version identification values include a user identifier for identifying a user that provided the first request.

5. The method of claim 1, wherein the first request to modify the entry is a request to update or delete the entry.

6. The method of claim 1, further comprising:
  receiving a third request to generate an additional entry corresponding to the respective numerically-versioned library;
  receiving user input defining data of the additional entry;
  generating a snapshot-parent record for the additional entry that includes data that does not change;
  generating a snapshot record for the additional entry that includes data that can be modified by a user; and
  assigning a respective plurality of version identification values to the snapshot record of the additional entry.

7. The method of claim 1, wherein the method further comprises:
  receiving a fourth request to approve a library version corresponding to the numerically-versioned library;
  obtaining a current library version record corresponding to the numerically-versioned library;
  updating a plurality of version identification values of the current library version record to identify the current library version record as approved;
  generating a new library version record corresponding to the numerically-versioned library, and
  assigning a respective plurality of version identification values to the new library version record such that the new library version record is identified as a draft.

8. The method of claim 7, wherein updating the plurality of version identification values of the previously-current library version record includes:
  assigning a start value of the respective plurality of version identification values of the new library version record as an end value for plurality of version identification values of the current library version record.

9. The method of claim 1, further comprising:
  receiving a fifth request to generate a new numerically-versioned library;
  in response to receiving the fifth request, generating the new numerically-versioned library;
  generating a respective library version record for the new numerically-versioned library;
  assigning a plurality of version identification values to the respective library version record;
  generating a respective library version under-master snapshot record corresponding to an entry of a master; and
  assigning a plurality of version identification values to the respective library version under-master snapshot record.

10. The method of claim 9, further comprising:
  determining whether additional entries are associated with the master; and
  in accordance with a determination that additional entries are associated with the master, for each additional entry:
    generating an additional respective library version under-master snapshot record; and
    assigning a respective plurality of version identification values to the additional respective library version under-master snapshot record.

11. The method of claim 10, further comprising:
  determining whether the new numerically-versioned library is to be pre-populated;
  in accordance with a determination that the library is to be pre-populated, importing an existing entry corresponding to another library record; and
  assigning a plurality of version identification values to the new, imported entry.

12. The method of claim 1, wherein a portion of the configuration data is shared among a subset of one or more numerically-versioned libraries under a related master.

13. A method of managing one or more records for a medical device, comprising:
  storing one or more masters associated with a medical device at an external database, the one or more masters comprising configuration data associated with programming the medical device;
  receiving a first request to modify an entry corresponding to a respective master;
  obtaining, responsive to receiving the first request, at least a first snapshot record for the entry, the first snapshot record including a first plurality of version identification values and a first data structure including a first version history such that a copy of the first snapshot is not created to change the respective master;
  receiving user changes to data of the entry;

generating, responsive to receiving the user changes, a second snapshot record for the entry that includes a second data structure including a second version history such that a copy of the second snapshot is not created to change the respective master, wherein generating the second snapshot record includes:
    capturing the user changes to the data of the entry, and
    assigning a second plurality of version identification values to the second snapshot record;
updating the first plurality of version identification values of the first snapshot record based on assigned values of the second plurality of version identification values of the second snapshot record such that the first snapshot record is identified as preceding the second snapshot record;
storing the first snapshot record and the second snapshot record in association with the respective master at the external database such that duplicate entries are not generated;
receiving, in connection with programming the medical device, a second request to access an entry of the respective master from the external database;
identifying one or more records corresponding to the entry of the respective master; and
providing, responsive to the second request, a copy of the one or more records corresponding to the entry of the respective master from the external database to the medical device to cause the programming of the medical device.

14. The method of claim 13, wherein the method further comprises:
    after generating the second snapshot record, generating a new library version under-master snapshot record for each numerically-versioned library that references the master, including, for each numerically-versioned library that references the master:
        receiving a current library version record for a numerically-versioned library,
        assigning a plurality of version identification values to the new library version under-master snapshot record based on the current library version record for the numerically-versioned library,
        assigning the new library version under-master snapshot record to the second snapshot record of the modified entry, and
        updating a plurality of version identification values of a previously-last library version under-master snapshot record, wherein the plurality of version identification values for the previously-last library version under-master snapshot record indicates that the previously-last library version under-master snapshot record precedes the new library version under-master snapshot record.

15. The method of claim 13, the method further comprises:
    after generating the snapshot record of an additional master entry, generating a new library version under-master snapshot record for each numerically-versioned library that references the master, including, for each numerically-versioned library that references the master:
        receiving a current library version record for a numerically-versioned library,
        assigning a plurality of version identification values to the new library version under-master snapshot record based on the current library version record for the numerically-versioned library, and
        assigning the new library version under-master snapshot record to the snapshot record of the additional entry.

16. A non-transitory computer readable medium storing one or more programs, the one or more programs comprising instructions, which when executed by a device, cause the device to:
    store one or more numerically-versioned libraries associated with a medical device at an external database, the one or more numerically-versioned libraries comprising configuration data associated with programming the medical device;
    receive a first request to modify an entry corresponding to a respective numerically-versioned library;
    obtain, responsive to receiving the first request, at least a first snapshot record included in the entry, the first snapshot record including a first plurality of version identification values and a first data structure including a first version history such that a copy of the first snapshot is not created to change the respective numerically-versioned library;
    receive user changes to data of the entry;
    generate, responsive to receiving the user changes, a second snapshot record for the entry that includes a second data structure including a second version history such that a copy of the second snapshot is not created to change the respective numerically-versioned library, wherein generating the second snapshot record includes:
        capture the user changes to the data of the entry, and
        assign a second plurality of version identification values to the second snapshot record;
    update the first plurality of version identification values of the first snapshot record based on assigned values of the second plurality of version identification values of the second snapshot record such that the first snapshot record is identified as preceding the second snapshot record;
    store the first snapshot record and the second snapshot record in association with the respective numerically-versioned library at the external database such that duplicate entries are not generated;
    receive, in connection with programming the medical device, a second request to access a numbered version of the respective numerically-versioned library from the external database;
    identify one or more records corresponding to the numbered version of the respective numerically-versioned library; and
    provide, responsive to the second request, a copy of the one or more record corresponding to the numbered version of the respective numerically-versioned library from the external database to the medical device to cause the programming of the medical device.

17. The non-transitory computer readable medium of claim 16, further comprising instructions, which when executed by a device, cause the device to:
    receiving a third request to generate an additional entry corresponding to the respective numerically-versioned library;
    receiving user input defining data of the additional entry;
    generating a snapshot-parent record for the additional entry that includes data that does not change;
    generating a snapshot record for the additional entry that includes data that can be modified by a user; and
    assigning a respective plurality of version identification values to the snapshot record of the additional entry.

18. The non-transitory computer readable medium of claim 16, further comprising instructions, which when executed by a device, cause the device to:
receiving a fourth request to approve a library version corresponding to the numerically-versioned library;
obtaining a current library version record corresponding to the numerically-versioned library;
updating a plurality of version identification values of the current library version record to identify the current library version record as approved;
generating a new library version record corresponding to the numerically-versioned library, and
assigning a respective plurality of version identification values to the new library version record such that the new library version record is identified as a draft.

19. A computer server system for managing one or more records, the computer server system comprising:
one or more processors; and
memory storing one or more instructions that, when executed by the one or more processors, cause the computer server system to perform operations including:
storing one or more numerically-versioned libraries associated with a medical device at an external database, the one or more numerically-versioned libraries comprising configuration data associated with programming the medical device;
receiving a first request to modify an entry corresponding to a respective numerically-versioned library;
obtaining, responsive to receiving the first request, at least a first snapshot record included in the entry, the first snapshot record including a first plurality of version identification values and a first data structure including a first version history such that a copy of the first snapshot is not created to change the respective numerically-versioned library;
receiving user changes to data of the entry;
generating, responsive to receiving the user changes, a second snapshot record for the entry that includes a second data structure including a second version history such that a copy of the second snapshot is not created to change the respective numerically-versioned library, wherein generating the second snapshot record includes:
capturing the user changes to the data of the entry, and
assigning a second plurality of version identification values to the second snapshot record;
updating the first plurality of version identification values of the first snapshot record based on assigned values of the second plurality of version identification values of the second snapshot record such that the first snapshot record is identified as preceding the second snapshot record;
storing the first snapshot record and the second snapshot record in association with the respective numerically-versioned library at the external database such that duplicate entries are not generated;
receiving, in connection with programming the medical device, a second request to access a numbered version of the respective numerically-versioned library from the external database;
identifying one or more records corresponding to the numbered version of the respective numerically-versioned library; and
providing, responsive to the second request, a copy of the one or more record corresponding to the numbered version of the respective numerically-versioned library from the external database to the medical device to cause the programming of the medical device.

20. The computer server system of claim 19, further comprising instructions, which when executed by the one or more processors, cause the computer server system to perform operations including:
receiving a third request to generate an additional entry corresponding to the respective numerically-versioned library;
receiving user input defining data of the additional entry;
generating a snapshot-parent record for the additional entry that includes data that does not change;
generating a snapshot record for the additional entry that includes data that can be modified by a user; and
assigning a respective plurality of version identification values to the snapshot record of the additional entry.

* * * * *